(12) United States Patent
Mizusawa

(10) Patent No.: US 9,563,040 B2
(45) Date of Patent: Feb. 7, 2017

(54) WIDE-ANGLE OPTICAL SYSTEM AND ENDOSCOPE

(71) Applicant: OLYMPUS CORPORATION, Tokyo (JP)

(72) Inventor: Masayuki Mizusawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/173,040

(22) Filed: Jun. 3, 2016

(65) Prior Publication Data

US 2016/0282591 A1    Sep. 29, 2016

Related U.S. Application Data

(63) Continuation of application No. PCT/JP2015/065990, filed on Jun. 3, 2015.

(30) Foreign Application Priority Data

Jul. 23, 2014 (JP) .................................. 2014-149683

(51) Int. Cl.
*G02B 17/00* (2006.01)
*G02B 13/18* (2006.01)
(Continued)

(52) U.S. Cl.
CPC .................. *G02B 13/06* (2013.01); *A61B 1/00* (2013.01); *A61B 1/00174* (2013.01);
(Continued)

(58) Field of Classification Search
CPC ............ A61B 1/00096; A61B 1/00183; A61B 1/00195; A61B 1/00163; G02B 17/08; G02B 23/243; G02B 9/12; G02B 13/0055; G02B 27/0977; G02B 17/061
(Continued)

(56) References Cited

U.S. PATENT DOCUMENTS 5,473,474 A * 12/1995 Powell .................. G02B 13/06
                                                                359/725
5,745,302 A *  4/1998 Ohno .................... G02B 15/17
                                                                359/689
(Continued)

FOREIGN PATENT DOCUMENTS

EP          2163933        3/2010
EP          2385406        9/2011
(Continued)

OTHER PUBLICATIONS

International Search Report, mailed Aug. 25, 2015, issued in corresponding International Application No. PCT/JP2015/065990.

*Primary Examiner* — Evelyn A Lester
(74) *Attorney, Agent, or Firm* — Andrews Kurth Kenyon LLP

(57) ABSTRACT

A wide-angle optical system includes a first group having negative and positive lenses, a second group having a catadioptric optical element, and a third group. The catadioptric optical element includes a first surface at an object side, a second surface at an image side, and a third surface. The first surface has a first transmission surface and a first reflection surface disposed therearound. The second surface has a second transmission surface and a second reflection surface disposed therearound. The third surface is a circular conical transmission surface that is disposed between the first surface and the second surface and an apex of which is located at the object side.

3 Claims, 32 Drawing Sheets

(51) Int. Cl.
*A61B 1/06* (2006.01)
*G02B 13/06* (2006.01)
*G02B 13/04* (2006.01)
*G02B 17/08* (2006.01)
*G02B 23/26* (2006.01)
*G02B 23/24* (2006.01)
*G02B 27/00* (2006.01)
*A61B 1/00* (2006.01)
*G02B 13/00* (2006.01)
*G02B 9/12* (2006.01)
*G02B 27/09* (2006.01)
*G02B 17/06* (2006.01)

(52) U.S. Cl.
CPC ............ *G02B 13/04* (2013.01); *G02B 13/18* (2013.01); *G02B 17/08* (2013.01); *G02B 17/0856* (2013.01); *G02B 23/243* (2013.01); *G02B 23/26* (2013.01); *G02B 27/0025* (2013.01); *A61B 1/00096* (2013.01); *A61B 1/00163* (2013.01); *A61B 1/00183* (2013.01); *A61B 1/00195* (2013.01); *G02B 9/12* (2013.01); *G02B 13/0055* (2013.01); *G02B 17/061* (2013.01); *G02B 27/0977* (2013.01)

(58) Field of Classification Search
USPC ............... 359/709–712, 726, 727, 732, 737, 359/741, 784; 600/160–173; 348/45
See application file for complete search history.

(56) References Cited

U.S. PATENT DOCUMENTS

| | | | | |
|---|---|---|---|---|
| 6,333,826 | B1* | 12/2001 | Charles | G02B 13/06 359/725 |
| 6,341,044 | B1* | 1/2002 | Driscoll, Jr. | G02B 13/06 348/E5.055 |
| 6,449,103 | B1* | 9/2002 | Charles | G02B 13/06 359/366 |
| 6,611,282 | B1* | 8/2003 | Trubko | G02B 13/06 348/36 |
| 7,929,219 | B2* | 4/2011 | Togino | A61B 1/00096 359/726 |
| 8,462,195 | B2* | 6/2013 | Yeh | G02B 13/06 348/36 |
| 2002/0012059 | A1* | 1/2002 | Wallerstein | G02B 13/06 348/335 |
| 2004/0254424 | A1* | 12/2004 | Simkulet | A61B 1/00096 600/176 |
| 2006/0238879 | A1* | 10/2006 | Togino | G02B 17/0804 359/637 |
| 2008/0247062 | A1 | 10/2008 | Mizusawa | |
| 2009/0082629 | A1* | 3/2009 | Dotan | A61B 1/00096 600/160 |
| 2010/0007969 | A1* | 1/2010 | Togino | G02B 13/06 359/725 |
| 2010/0091385 | A1 | 4/2010 | Togino | |
| 2011/0279915 | A1 | 11/2011 | Mizusawa | |
| 2015/0265136 | A1 | 9/2015 | Honda | |

FOREIGN PATENT DOCUMENTS

| | | |
|---|---|---|
| EP | 2929830 | 10/2015 |
| JP | 2008-257121 | 10/2008 |
| JP | 2008-309861 | 12/2008 |
| JP | 2010-224010 | 10/2010 |
| JP | 2D18-255820 | 12/2013 |
| WO | 2008/153114 | 12/2008 |
| WO | 2010/084914 | 7/2010 |
| WO | 2014/088076 | 6/2014 |

* cited by examiner

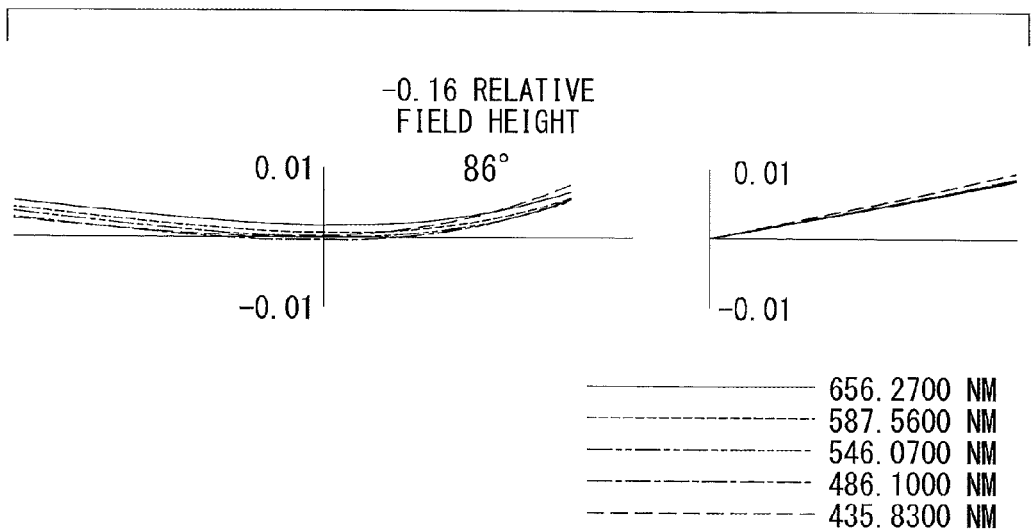
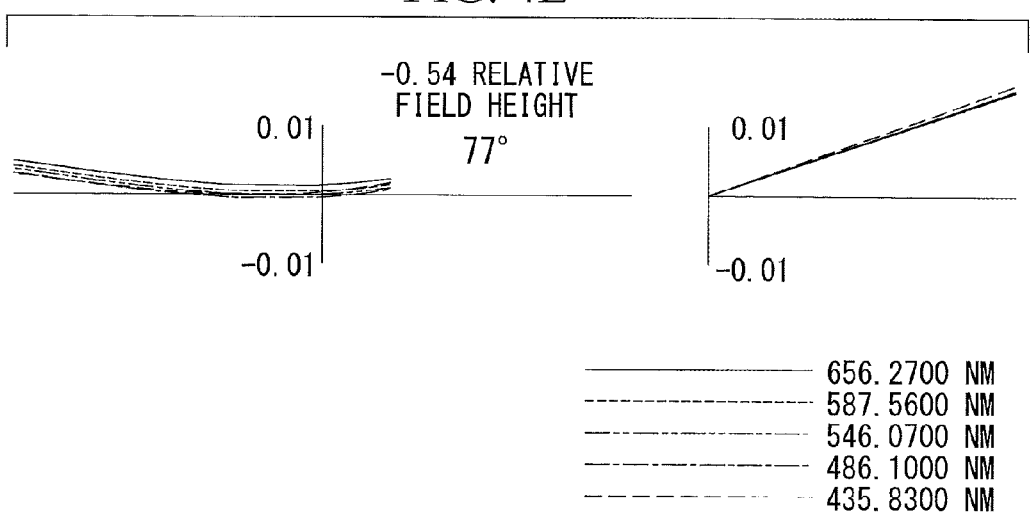

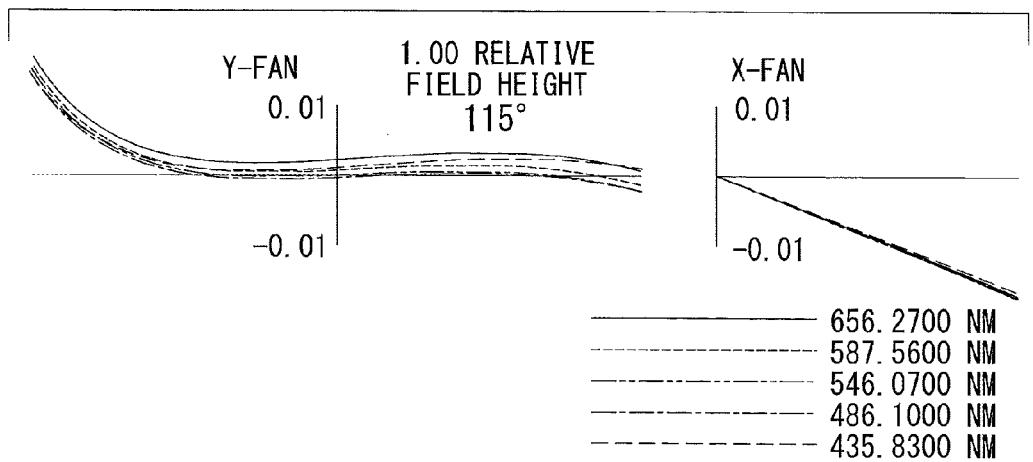
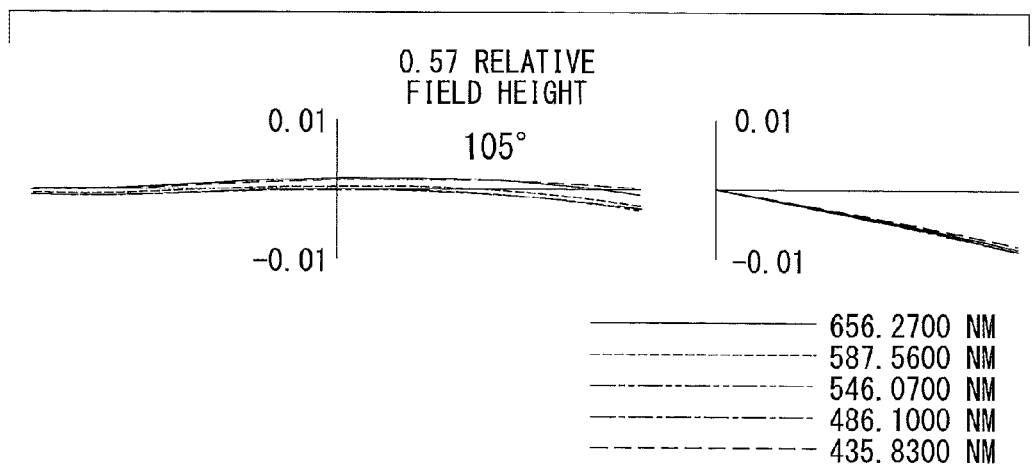

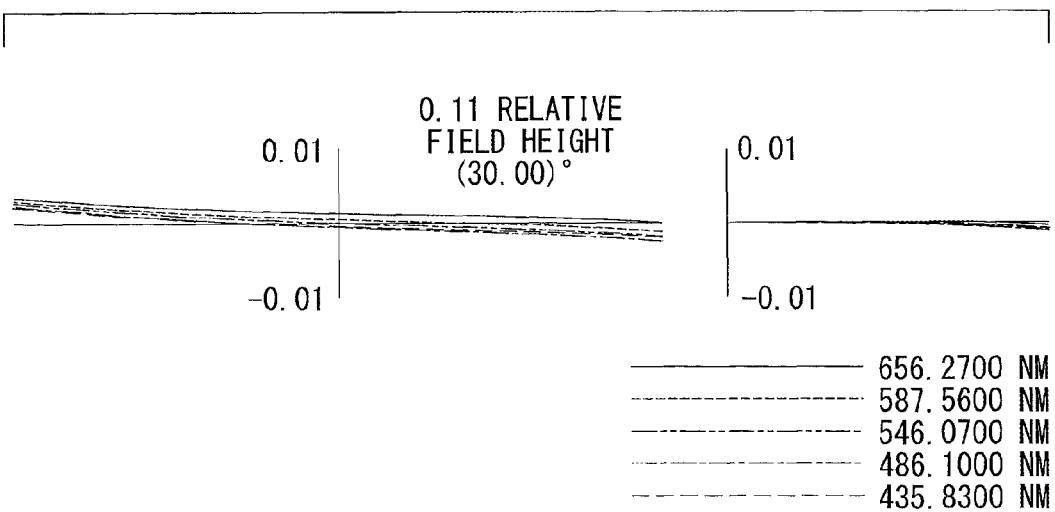
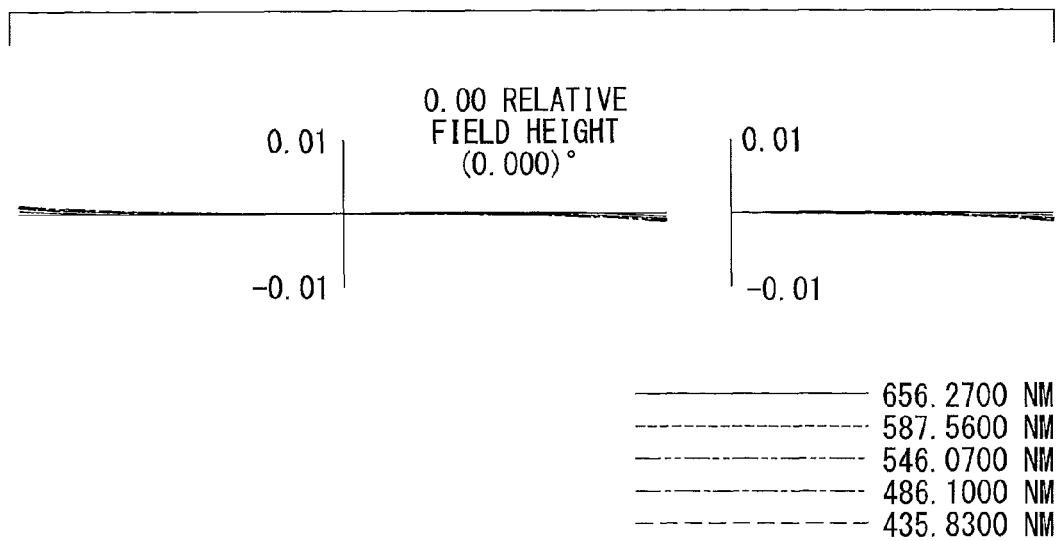

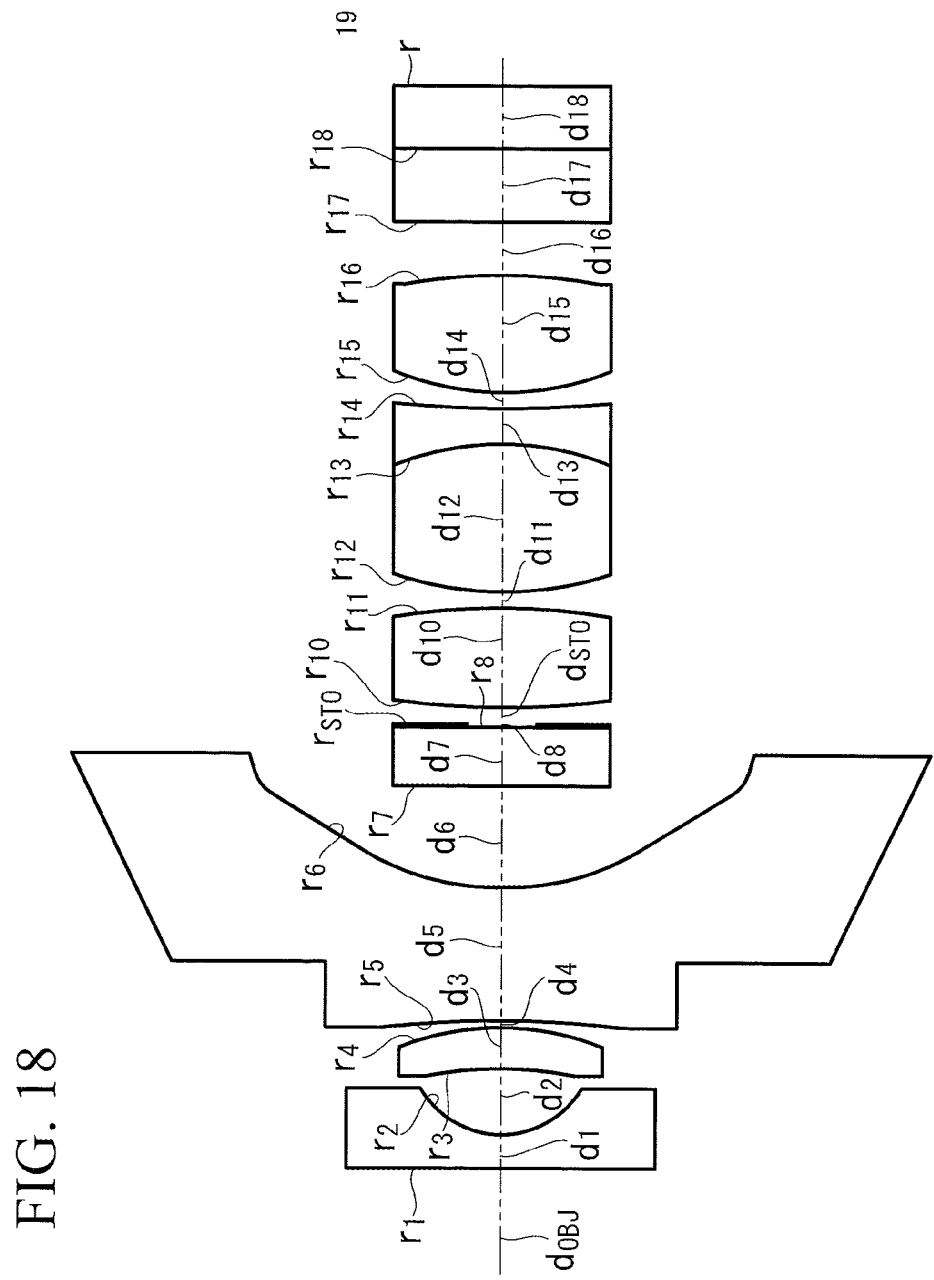

WIDE-ANGLE OPTICAL SYSTEM AND ENDOSCOPE

CROSS REFERENCE TO RELATED APPLICATIONS

This is a continuation of International Application PCT/JP/2015/065990, with an international filing date of Jun. 3, 2015, which is hereby incorporated by reference herein in its entirety. This application claims the benefit of Japanese Patent Application No. 2014-149683, the content of which is incorporated herein by reference.

TECHNICAL FIELD

The present invention relates to wide-angle optical systems and endoscopes.

BACKGROUND ART

A known optical system includes a first optical element having negative refractive power and a second optical element having positive refractive power. The first optical element causes forward light to be transmitted therethrough and causes lateral light to be reflected at a reflection surface located at the image side. The second optical element combines the two light paths from the front and lateral directions via the first optical element so as to form images thereof on a single image acquisition element. The optical system thus has a super-wide field angle so that both forward and lateral images can be observed at the same time (for example, see Patent Literatures 1 and 2).

In the optical system in Patent Literature 1, lateral light is refracted after being incident on a cylindrical surface of the first optical element, is sequentially reflected once at the reflection surface located at the image side and once at a reflection surface located at the object side opposite from the image side, and is subsequently transmitted through a transmission surface provided near the central axis at the image side so as to be incident on a positive optical element.

In Patent Literature 2, lateral light reflected only once at the reflection surface at the image side of the first optical element and forward light refracted after coming from the object side and transmitted through the transmission surface at the image side are incident on the positive optical element.

CITATION LIST

Patent Literature

{PTL 1}
Japanese Unexamined Patent Application, Publication No. 2008-309861
{PTL 2}
Japanese Unexamined Patent Application, Publication No. 2008-257121

SUMMARY OF INVENTION

Technical Problem

The present invention provides a wide-angle optical system and an endoscope in which lateral chromatic aberration can be sufficiently corrected by a single optical element in a subsequent stage while aligning the directions of images in all fields of view.

Solution to Problem

As aspect of the present invention provides a wide-angle optical system including a first group having a negative lens with negative refractive power and a positive lens with positive refractive power; a second group having a catadioptric optical element disposed at an image side of the first group; and a third group having positive refractive power and disposed at the image side of the second group. The catadioptric optical element includes a first surface disposed at an object side, a second surface disposed at the image side, and a third surface. The first surface includes a first transmission surface having an optical axis in the center thereof and a first reflection surface that is disposed in a ring shape around the first transmission surface and that reflects light from the image side. The second surface includes a second transmission surface having an optical axis in the center thereof and a second reflection surface that is disposed in a ring shape around the second transmission surface and that reflects light from the object side. The third surface is a circular conical transmission surface that is disposed between the first surface and the second surface and an apex of which is located at the object side.

Expressions (1), (2), and (3) below are satisfied:

$$\nu n > \nu p \quad (1)$$

$$|\phi n| > |\phi p| \quad (2)$$

$$\alpha/2 > 90° - \theta k \quad (3)$$

where $\nu n$ denotes an Abbe number of the negative lens, $\nu p$ denotes an Abbe number of the positive lens, $\phi n$ denotes the refractive power of the negative lens, $\phi p$ denotes the refractive power of the positive lens, $\alpha$ denotes an apex angle of the third surface, and $\theta k$ denotes a half field angle of a principal ray at a minimum field angle within a lateral field of view and satisfies $0° < \theta k < 90°$.

BRIEF DESCRIPTION OF DRAWINGS

FIG. 4D is an aberration diagram of light from a lateral object in the wide-angle optical system in FIG. 3 and illustrates a case where the half field angle of a principal ray at the minimum field angle is 86°.

FIG. 4E is an aberration diagram of light from a lateral object in the wide-angle optical system in FIG. 3 and illustrates a case where the half field angle of a principal ray at the minimum field angle is 77°.

FIG. 7A is an aberration diagram of light from a lateral object in the wide-angle optical system in FIG. 6 and illustrates a case where the half field angle of a principal ray at the minimum field angle is 115°.

FIG. 7B is an aberration diagram of light from a lateral object in the wide-angle optical system in FIG. 6 and illustrates a case where the half field angle of a principal ray at the minimum field angle is 105°.

FIG. 7C is an aberration diagram of light from a lateral object in the wide-angle optical system in FIG. 6 and illustrates a case where the half field angle of a principal ray at the minimum field angle is 95°.

FIG. 17D is an aberration diagram of light from a front object in the wide-angle optical system in FIG. 15 and illustrates a case where the half field angle of a principal ray at the minimum field angle is 30°.

FIG. 17E is an aberration diagram of light from a front object in the wide-angle optical system in FIG. 15 and illustrates a case where the half field angle of a principal ray at the minimum field angle is 0°.

FIG. 18 illustrates the lens arrangement in a sixth example of the wide-angle optical system in FIG. 2.

DESCRIPTION OF EMBODIMENTS

An endoscope 1 and a wide-angle optical system 3 according to a first embodiment of the present invention will be described below with reference to the drawings.

Figure 1:
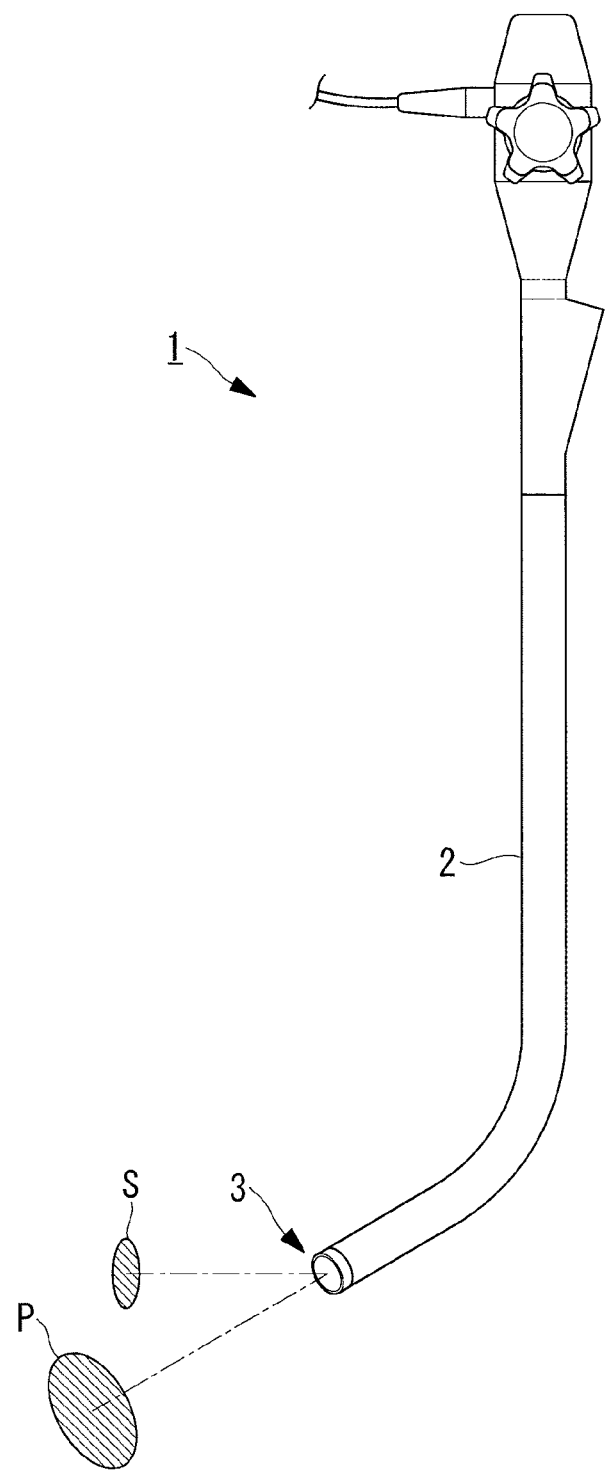
FIG. 1 is an overall view of an endoscope according to an embodiment of the present invention.

As shown in FIG. 1, the endoscope 1 according to this embodiment includes a narrow, flexible insertion section 2 to be inserted into a body and the wide-angle optical system 3 that is provided at the distal end of the insertion section 2 and that acquires images of front and lateral objects P and S.

Figure 2:
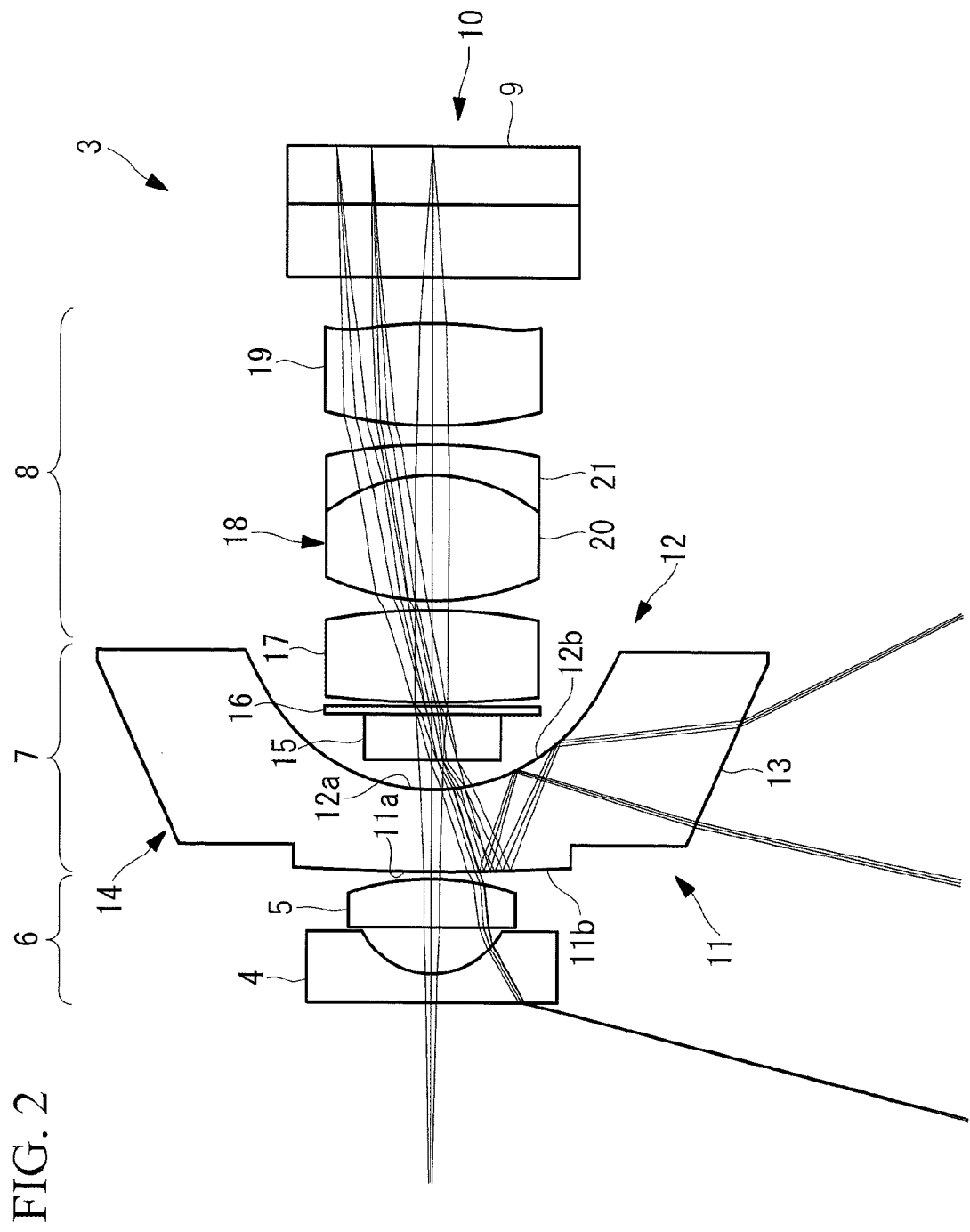
FIG. 2 illustrates the configuration of a wide-angle optical system according to an embodiment of the present invention.

As shown in FIG. 2, the wide-angle optical system 3 according to this embodiment includes, in the following order from the front object P side, a first group 6 that focuses forward light, a second group 7 that receives the light focused by the first group 6 and lateral light, a third group 8 that focuses the light entering from the two directions and passing through the second group 7, and an image acquisition element 10 having an image acquisition surface 9.

The first group 6 includes a negative lens 4 disposed at the object P side and having negative refractive power and a positive lens 5 disposed at the image side relative to the negative lens 4 and having positive refractive power.

The negative lens 4 is a plano-concave lens having a concave surface disposed at the image side, and the positive lens 5 is a plano-convex lens having a convex surface at the image side.

The negative lens 4 and the positive lens 5 satisfy the following conditional expressions (1) and (2):

$$\nu n > \nu p \qquad (1)$$

$$|\phi n| > |\phi p| \qquad (2)$$

where $\nu n$ denotes the Abbe number of the negative lens 4, $\nu p$ denotes the Abbe number of the positive lens 5, $\phi n$ denotes the refractive power of the negative lens 4, and ϕp denotes the refractive power of the positive lens 5.

The second group 7 includes: a catadioptric optical element 14 having a first surface 11 disposed at the front object P side, a second surface 12 disposed at the image side, and a third surface 13 disposed between the first surface 11 and the second surface 12; a parallel plate 15; an aperture stop 16 disposed at the image side of the parallel plate 15; and a biconvex lens 17.

The first surface 11 includes a substantially-circular first transmission surface 11a in which the optical axis is disposed in the center thereof and that transmits the light coming from the first group 6, and also includes a first reflection surface 11b that is disposed in a substantially ring shape around the first transmission surface 11a and that internally reflects the light coming from the image side.

The second surface 12 includes a substantially-circular second transmission surface 12a in which the optical axis is disposed in the center thereof and that transmits the light transmitted through the first transmission surface 11a and the light internally reflected at the first reflection surface 11b, and also includes a second reflection surface 12b that is disposed in a substantially ring shape around the second transmission surface 12a and that internally reflects the light. The internal reflection at the second reflection surface 12b is total reflection.

The third surface 13 is a circular conical surface with its apex located at the front object P side and is configured to transmit lateral light.

The apex angle of the third surface 13 satisfies the following conditional expression (3):

$$\alpha/2 > 90° - \theta k \qquad (3)$$

where α denotes the apex angle of the third surface 13, and θk denotes a half field angle of a principal ray at the minimum field angle within the lateral field of view and satisfies 0°<θk<90°.

The light coming from the lateral object S and transmitted through the third surface 13 is refracted at the third surface 13, is subsequently internally reflected at the second reflection surface 12b of the second surface 12, is further internally reflected at the first reflection surface 11b of the first surface 11, and is transmitted through the second transmission surface 12a of the second surface 12. A portion of this light passing through the parallel plate 15 and the aperture stop 16 is focused by the biconvex lens 17 so as to enter the third group 8.

The third group 8 is a lens group having positive refractive power and including a compound lens 18 that receives the light passing through the aperture stop 16. Reference sign 19 denotes another lens that constitutes the third group 8.

The compound lens 18 is formed by joining together a biconvex lens 20, which is disposed at the object P side, and a meniscus lens 21.

The operation of the endoscope 1 and the wide-angle optical system 3 according to this embodiment, having the above-described configuration, will be described below.

In order to observe the front and lateral objects P and S by using the endoscope 1 according to this embodiment, the distal end of the insertion section 2 is disposed facing the front object P.

Forward light enters the first group 6 of the wide-angle optical system 3, is transmitted through the first group 6 so as to become incident on the first transmission surface 11a of the first surface 11 of the catadioptric optical element 14 in the second group 7, and is transmitted through the catadioptric optical element 14 so as to be output toward the third group 8 from the second transmission surface 12a of the second surface 12.

Because the first group 6 is set such that the Abbe number of the negative lens 4 is larger than the Abbe number of the positive lens 5, as indicated in expression (1), the occurrence of lateral chromatic aberration in the negative lens 4 can be suppressed. Because the first group 6 has negative refractive power overall, as indicated in expression (2), the first group 6 can focus light from a wide forward range.

Lateral light becomes incident on the third surface 13 of the catadioptric optical element 14 in the second group 7. Because the lateral light satisfies expression (3), all principal rays to be incident on the third surface 13 become incident on the third surface 13 from the image side relative to the normal thereto.

Accordingly, all principal rays incident on the third surface 13 from the lateral direction are refracted toward the image side so that lateral chromatic aberrations occurring due to the refraction can be given the same sign, which is also the same as the sign of lateral chromatic aberration occurring in the light from the front object P. The lateral light refracted toward the image side in the third surface 13 is internally reflected twice at the second reflection surface 12b of the second surface 12 and the first reflection surface 11b of the first surface 11 in this order and is subsequently output toward the third group 8 from the second transmission surface 12a of the second surface 12.

Specifically, after passing through the second group 7, the two rays of forward light and lateral light pass through the single third group 8 so that images thereof are acquired by the image acquisition element 10.

Accordingly, the wide-angle optical system 3 according to this embodiment is advantageous in that, when the two rays of forward light and lateral light are output from the second group 7, the lateral chromatic aberrations have the same sign so that the lateral chromatic aberrations of all light rays can be corrected by the single third group 8.

Since the light from the lateral object S is internally reflected twice within the catadioptric optical element 14, the image is prevented from being vertically inverted. This is advantageous in that the directions of images in all fields of view can be aligned.

In this embodiment, the first group 6 has the negative lens 4 and the positive lens 5, which are arranged in this order from the object P side. Alternatively, the order in which the positive lens 5 and the negative lens 4 are arranged may be interchanged.

The wide-angle optical system 3 preferably satisfies the following expression (4).

$$\nu n > 35 > \nu p \qquad (4)$$

As a result, this makes it easier to suppress lateral chromatic aberration occurring in the negative lens 4.

In this embodiment, the second reflection surface 12b is configured to totally reflect the light coming from the lateral object S and transmitted through the third surface 13. Alternatively, the inner surface of the second reflection surface 12b may be mirror-coated.

Next, a first example of the wide-angle optical system 3 according to this embodiment will be described below with reference to FIGS. 3 to 5E and lens data.

Figure 3:
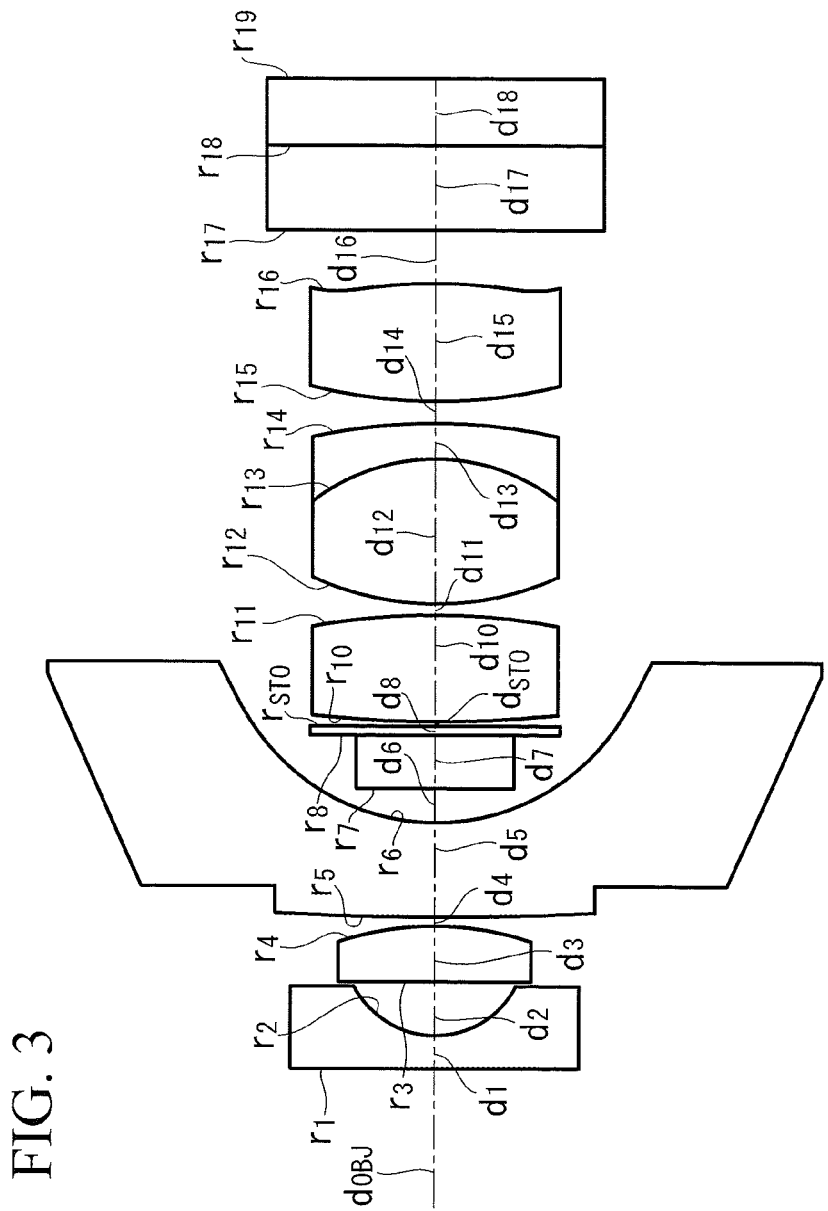
FIG. 3 illustrates the lens arrangement in a first example of the wide-angle optical system in FIG. 2.
Figure 4A:
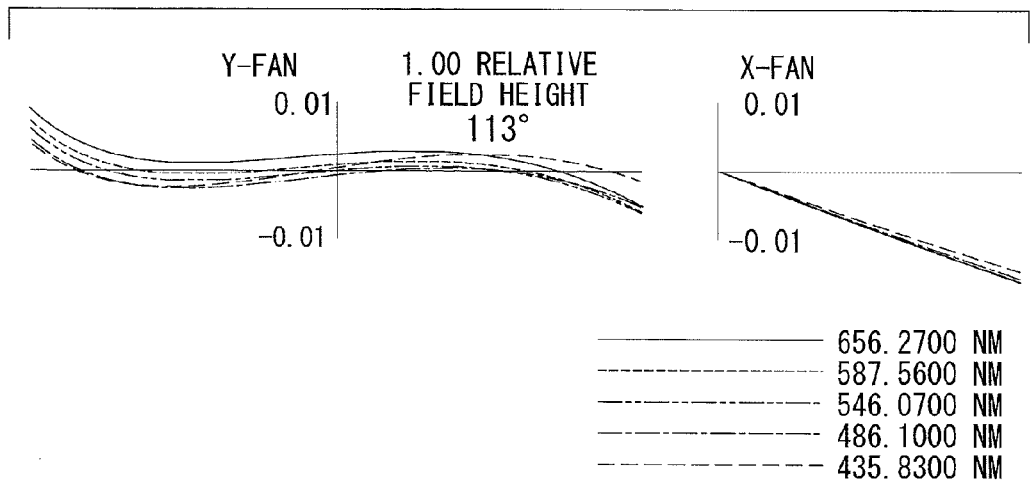
FIG. 4A is an aberration diagram of light from a lateral object in the wide-angle optical system in FIG. 3 and illustrates a case where the half field angle of a principal ray at the minimum field angle is 113°.
Figure 4B:
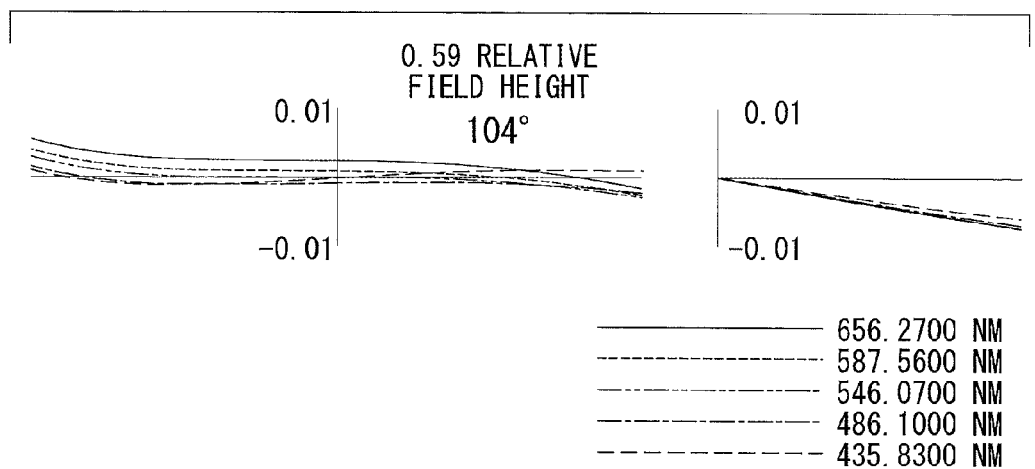
FIG. 4B is an aberration diagram of light from a lateral object in the wide-angle optical system in FIG. 3 and illustrates a case where the half field angle of a principal ray at the minimum field angle is 104°.
Figure 4C:
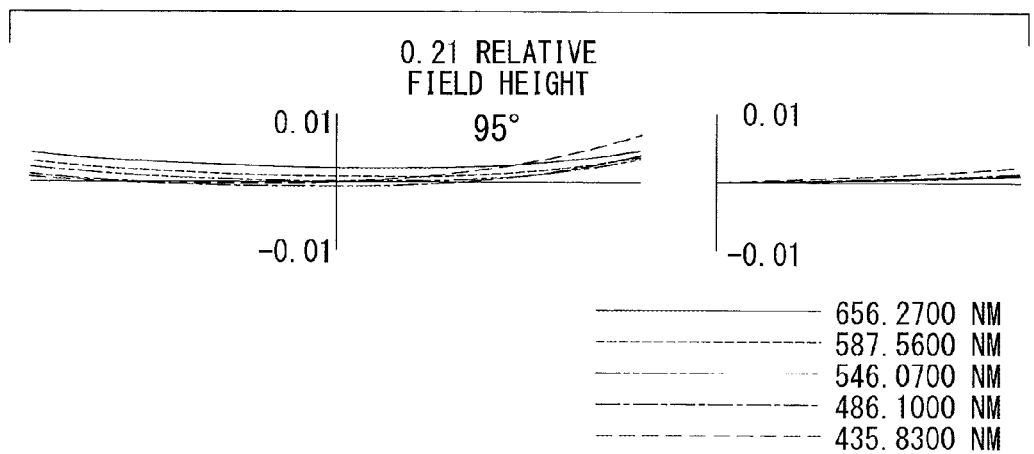
FIG. 4C is an aberration diagram of light from a lateral object in the wide-angle optical system in FIG. 3 and illustrates a case where the half field angle of a principal ray at the minimum field angle is 95°.
Figure 5A:
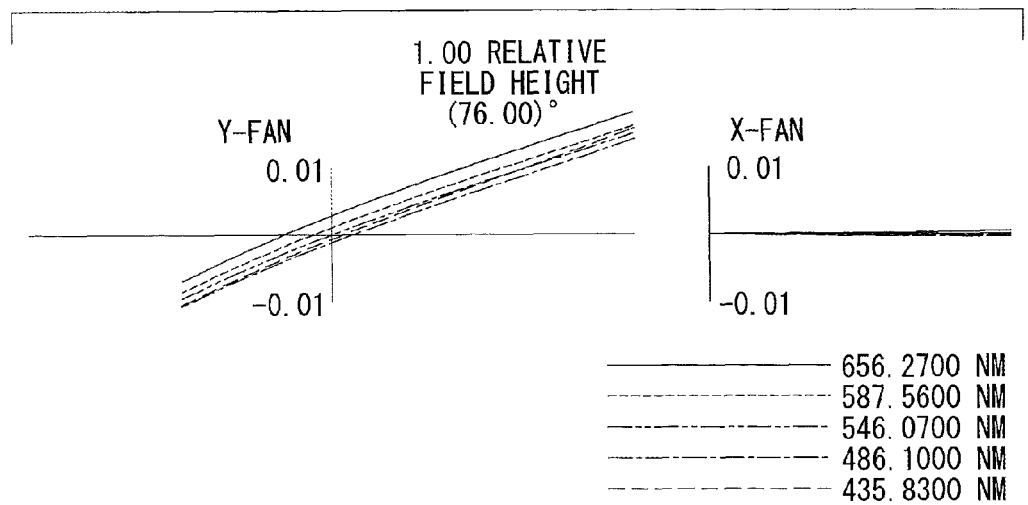
FIG. 5A is an aberration diagram of light from a front object in the wide-angle optical system in FIG. 3 and illustrates a case where the half field angle of a principal ray at the minimum field angle is 76°.
Figure 5B:
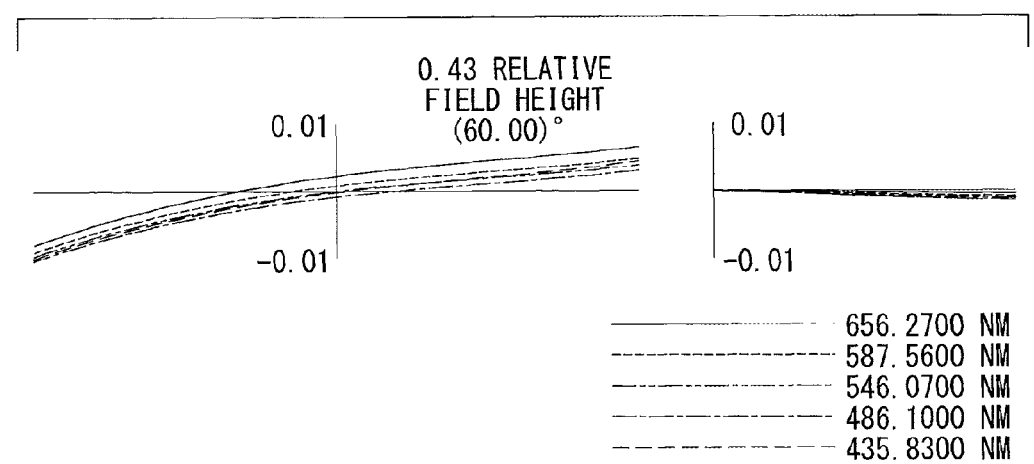
FIG. 5B is an aberration diagram of light from a front object in the wide-angle optical system in FIG. 3 and illustrates a case where the half field angle of a principal ray at the minimum field angle is 60°.
Figure 5C:
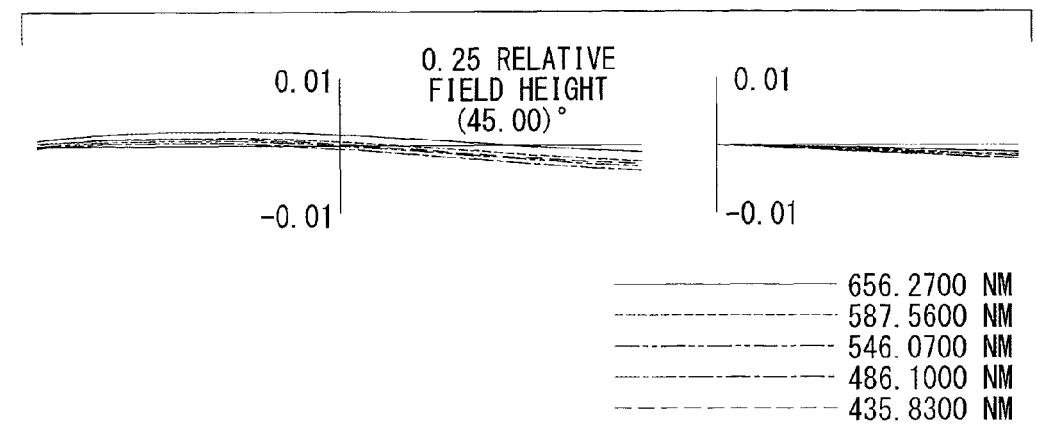
FIG. 5C is an aberration diagram of light from a front object in the wide-angle optical system in FIG. 3 and illustrates a case where the half field angle of a principal ray at the minimum field angle is 45°.
Figure 5D:
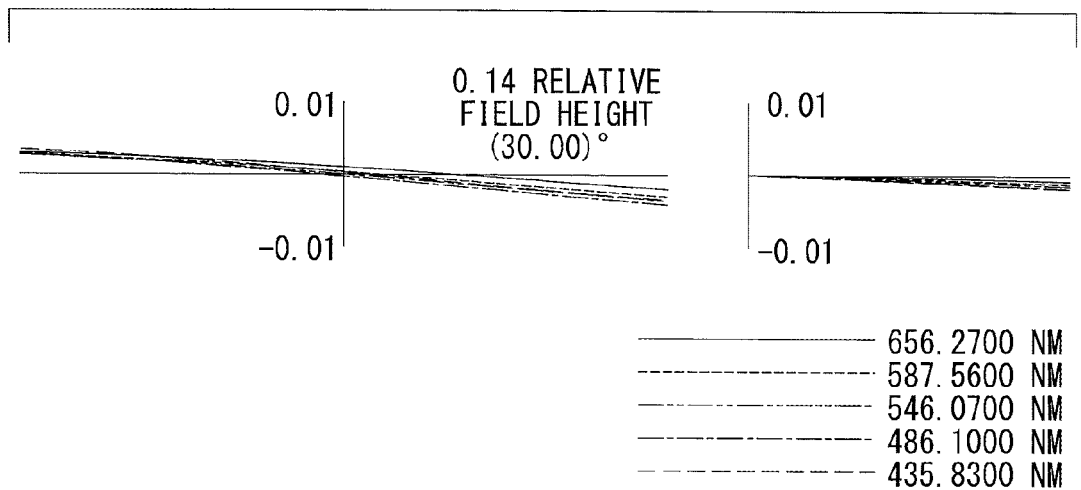
FIG. 5D is an aberration diagram of light from a front object in the wide-angle optical system in FIG. 3 and illustrates a case where the half field angle of a principal ray at the minimum field angle is 30°.
Figure 5E:
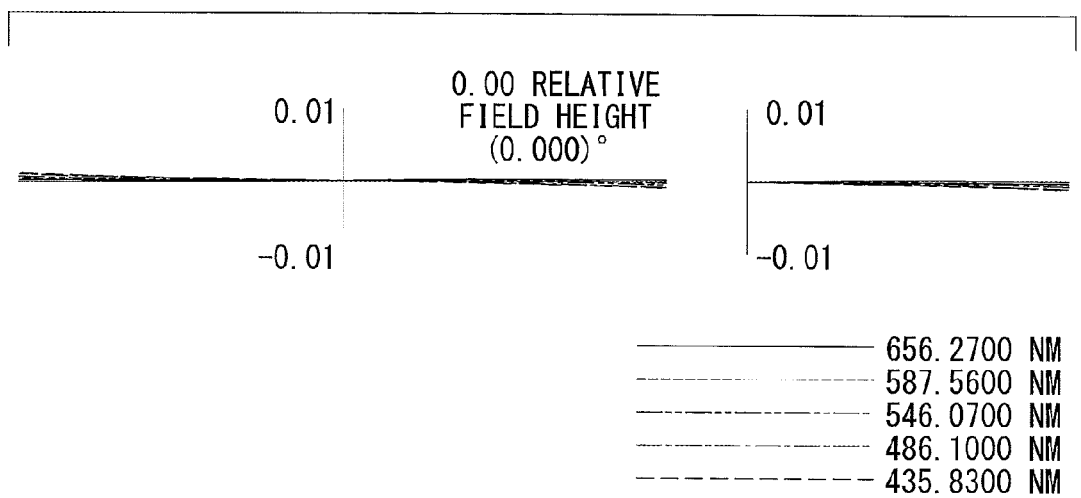
FIG. 5E is an aberration diagram of light from a front object in the wide-angle optical system in FIG. 3 and illustrates a case where the half field angle of a principal ray at the minimum field angle is 0°.

FIG. 3 illustrates the lens arrangement of the wide-angle optical system 3 according to this example. FIGS. 4A to 5E illustrate aberration diagrams of the lens arrangement according to this example. In each diagram, the X direction indicates lateral chromatic aberration, whereas the Y direction indicates comatic aberration.

In the lens data below, r denotes the radius of curvature (mm), d denotes the distance between surfaces (mm), ν denotes the Abbe number, Nd denotes the refractive index with respect to the d-line, OBJ denotes an object (i.e., the front object P), and IMG denotes the image acquisition surface 9. In the lens data, the symbol * denotes an aspherical lens.

| Surface No. | r | d | ν | Nd |
|---|---|---|---|---|
| OBJ | ∞ | 4.878144 | | |
| 1 | ∞ | 0.286885 | 40.8 | 1.8830 |
| 2 | 0.82194 | 0.483607 | | |
| 3 | ∞ | 0.475288 | 17.4 | 1.9591 |
| 4 | −2.70744 | 0.081967 | | |
| 5 | −7.77656 | 0.803279 | 64.1 | 1.5163 |
| 6 | 1.53360 | 0.327869 | | |
| 7 | ∞ | 0.491803 | 46.6 | 1.8160 |
| 8 | ∞ | 0.024590 | | |
| STO | ∞ | 0.000000 | | |
| 10 | 12.29508 | 0.948401 | 46.6 | 1.8160 |
| 11 | −4.56082 | 0.081967 | | |
| 12 | 2.62295 | 1.270492 | 54.7 | 1.7292 |
| 13 | −1.77686 | 0.327869 | 17.4 | 1.9591 |
| 14 | −4.72357 | 0.183674 | | |
| 15 | 4.29340 | 1.024590 | 40.9 | 1.8061 |
| 16* | −4.64897 | 0.491803 | | |
| 17 | ∞ | 0.737705 | 64.1 | 1.5163 |
| 18 | ∞ | 0.573770 | 64.1 | 1.5163 |
| 19 | ∞ | 0.000000 | | |
| IMG | ∞ | 0.000000 | | |

Aspherical Data
Fifth Surface
K=0.000000, A4=0.181585E+00, A6=−0.170990E+00, A8=0.292551E-01, A10=0.350339E-01
Sixth Surface
K=−0.484012, A4=0.356447E-01, A6=0.300682E-01, A8=−0.261528E-01, A10=0.609574E-02
Sixteenth Surface
K=0.000000, A4=0.413814E-01, A6=0.353986E-02, A8=0.553823E-01, A10=−0.364465E-01

The values in this example are as follows. In the following, fn denotes the focal length (mm) of the negative lens 4, and fp denotes the focal length (mm) of the positive lens. Accordingly, it is clear that conditional expressions (1) to (4) are satisfied.

$fn = -0.925$ $fp = 2.786$ $\phi n = -1.801$ $\phi p = 0.359$ $\nu n = 40.8$ $\nu p = 17.4$ $|\phi n|/\nu n = 0.026$ $|\phi p|/\nu p = 0.021$ $(|\phi n|/\nu n)/(|\phi p|/\nu p) = 1.284$ $\alpha = 46°$ The apex α is located 4.77 (mm) away from the first surface 11 toward the front object P side.

In this example, the maximum half field angle of the light from the front object P is 76°, the half field angle of the principal ray from the lateral object S ranges between 76° and 116°, the focal length (forward light path) is 0.569 mm, the F number (forward light path) is 5.0, the maximum image height is 1.0 mm, and the maximum forward image height is 0.609 mm.

Next, a second example of the wide-angle optical system 3 according to this embodiment will be described below with reference to FIGS. 6 to 8E and lens data.

Figure 6:
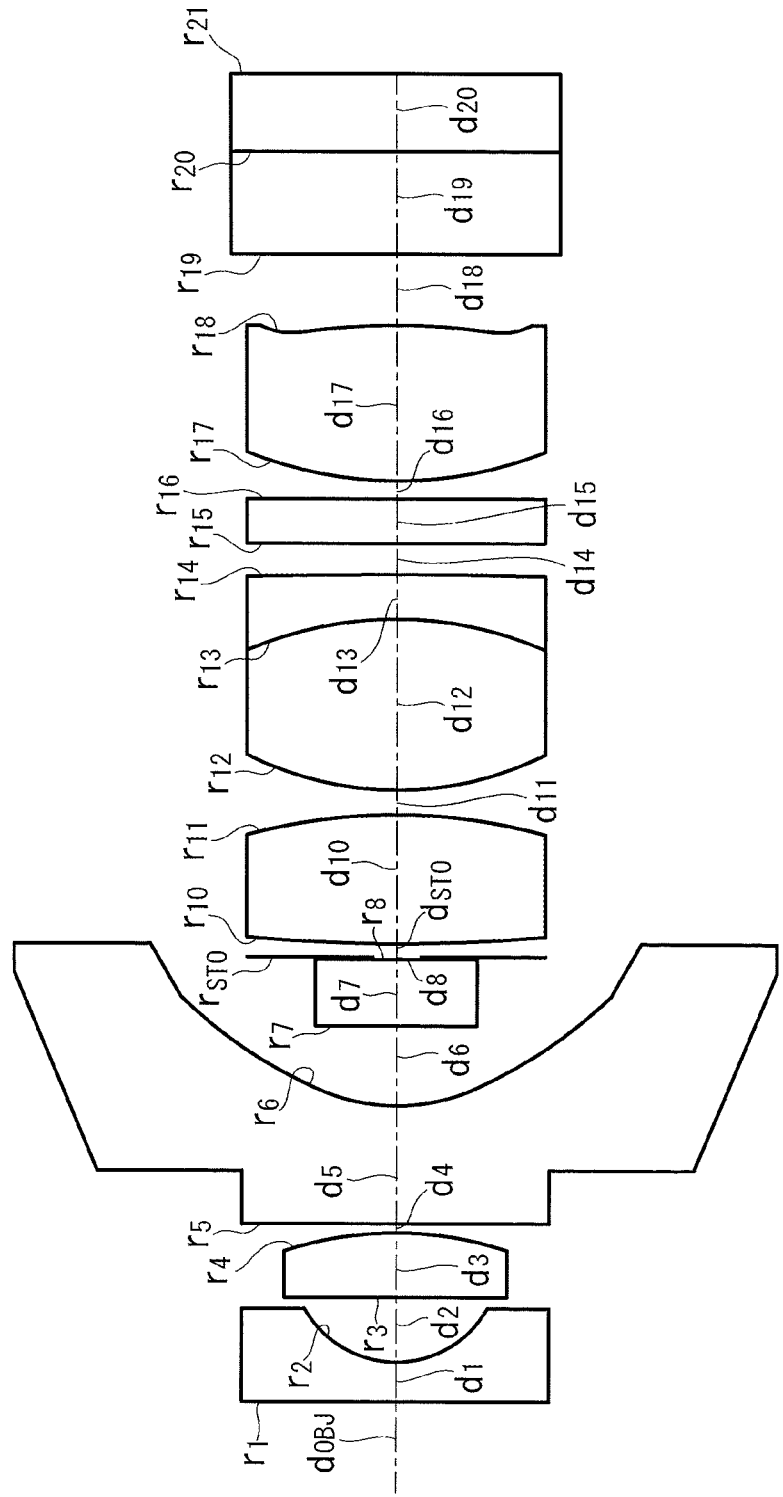
FIG. 6 illustrates the lens arrangement in a second example of the wide-angle optical system in FIG. 2.
Figure 7D:
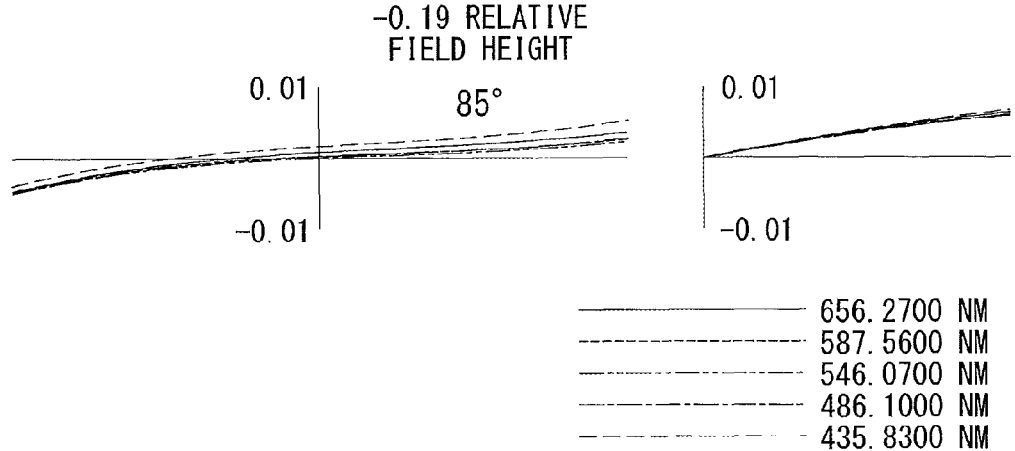
FIG. 7D is an aberration diagram of light from a lateral object in the wide-angle optical system in FIG. 6 and illustrates a case where the half field angle of a principal ray at the minimum field angle is 85°.
Figure 7E:
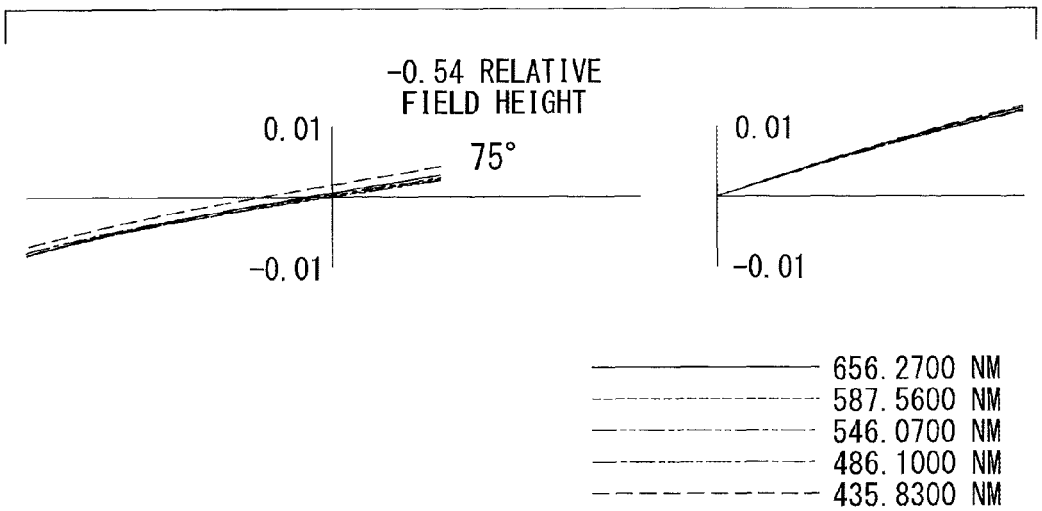
FIG. 7E is an aberration diagram of light from a lateral object in the wide-angle optical system in FIG. 6 and illustrates a case where the half field angle of a principal ray at the minimum field angle is 75°.
Figure 8A:
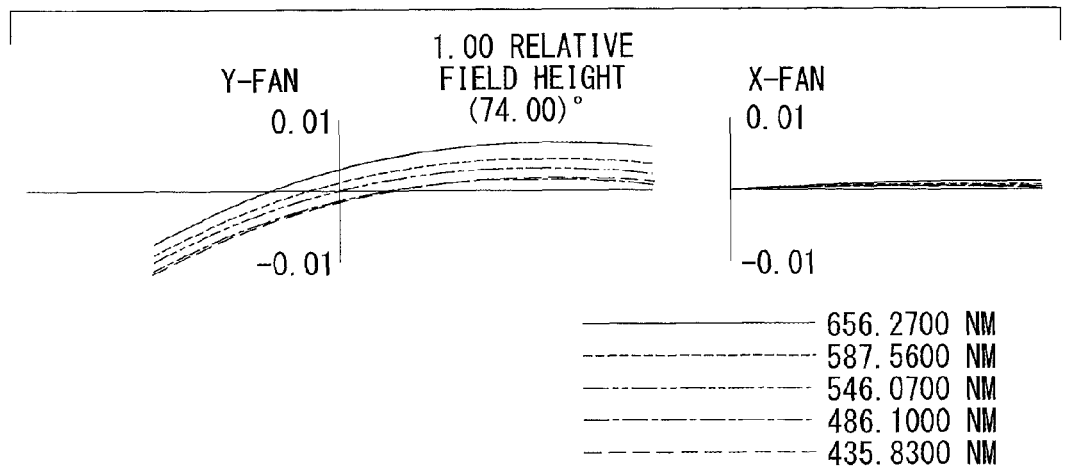
FIG. 8A is an aberration diagram of light from a front object in the wide-angle optical system in FIG. 6 and illustrates a case where the half field angle of a principal ray at the minimum field angle is 74°.
Figure 8B:
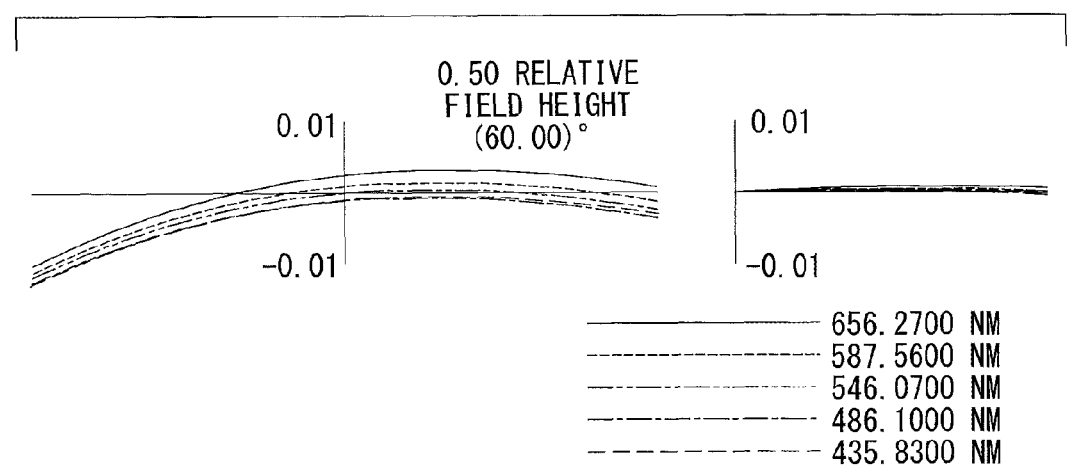
FIG. 8B is an aberration diagram of light from a front object in the wide-angle optical system in FIG. 6 and illustrates a case where the half field angle of a principal ray at the minimum field angle is 60°.
Figure 8C:
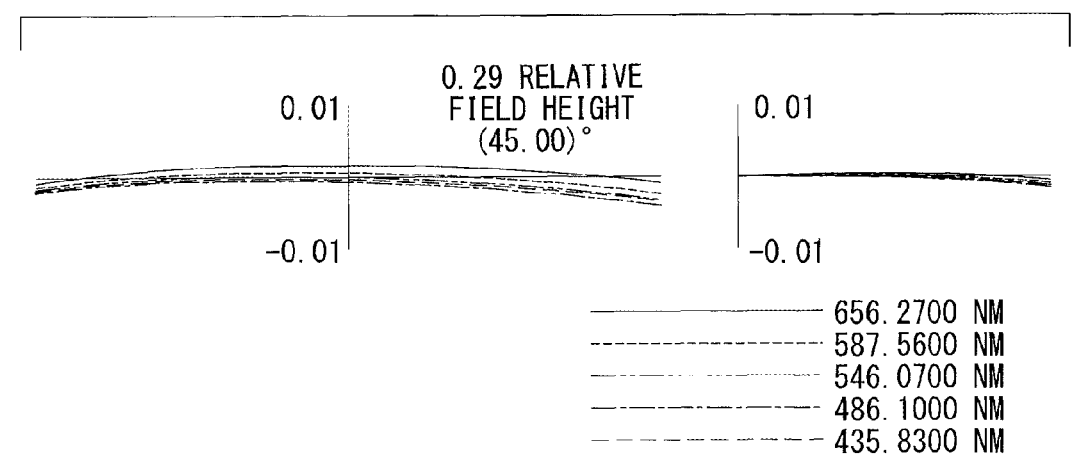
FIG. 8C is an aberration diagram of light from a front object in the wide-angle optical system in FIG. 6 and illustrates a case where the half field angle of a principal ray at the minimum field angle is 45°.
Figure 8D:
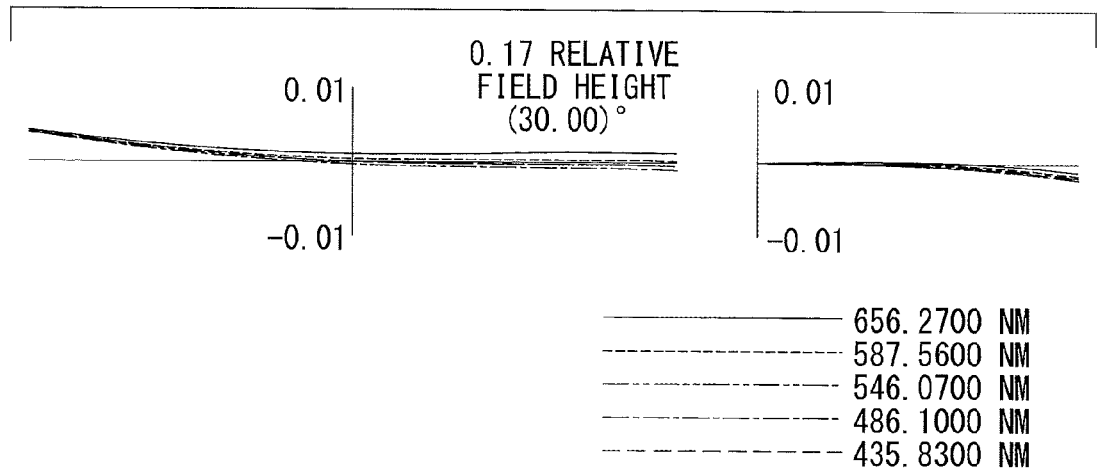
FIG. 8D is an aberration diagram of light from a front object in the wide-angle optical system in FIG. 6 and illustrates a case where the half field angle of a principal ray at the minimum field angle is 30°.
Figure 8E:
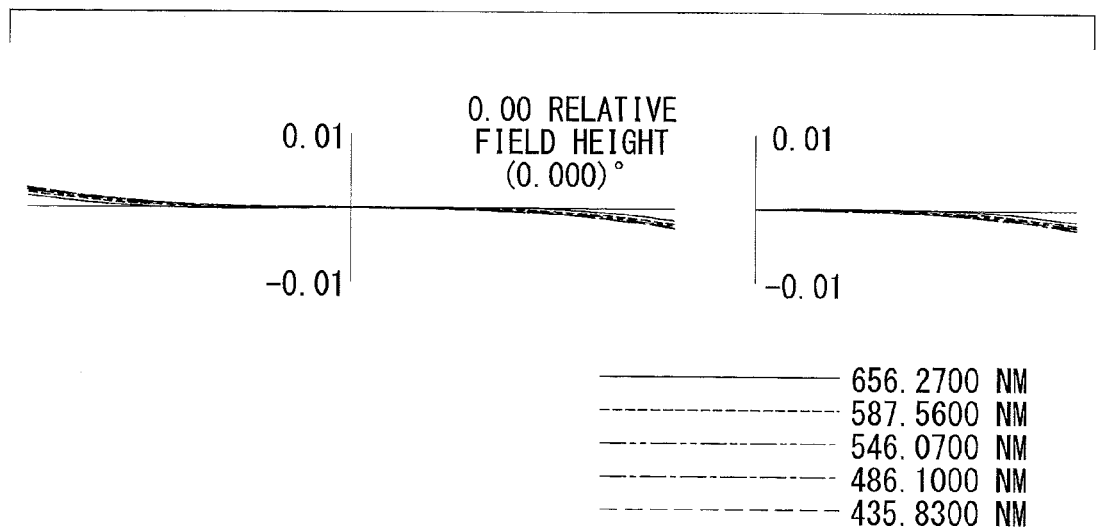
FIG. 8E is an aberration diagram of light from a front object in the wide-angle optical system in FIG. 6 and illustrates a case where the half field angle of a principal ray at the minimum field angle is 0°.

FIG. 6 illustrates the lens arrangement of the wide-angle optical system 3 according to this example. FIGS. 7A to 8E illustrate aberration diagrams of the wide-angle optical system 3 according to this example. In each diagram, the X direction indicates lateral chromatic aberration, whereas the Y direction indicates comatic aberration.

| Surface No. | r | d | ν | Nd |
|---|---|---|---|---|
| OBJ | ∞ | 4.066102 | | |
| 1 | ∞ | 0.286885 | 40.8 | 1.8830 |
| 2 | 0.79205 | 0.467213 | | |
| 3 | ∞ | 0.468048 | 18.9 | 1.9343 |
| 4 | −2.84888 | 0.081967 | | |
| 5* | −21.31148 | 0.870556 | 64.1 | 1.5163 |
| 6* | 1.12433 | 0.567778 | | |
| 7 | ∞ | 0.491803 | 64.1 | 1.5163 |
| 8 | ∞ | 0.024590 | | |
| STO | ∞ | 0.087009 | | |
| 10 | 12.29508 | 0.948401 | 46.6 | 1.8160 |
| 11 | −4.49367 | 0.170697 | | |
| 12 | 2.32825 | 1.270492 | 54.7 | 1.7292 |
| 13 | −2.73661 | 0.327869 | 18.9 | 1.9343 |
| 14 | −28.22847 | 0.233287 | | |
| 15 | ∞ | 0.327869 | 64.1 | 1.5163 |
| 16 | ∞ | 0.118685 | | |
| 17 | 2.87047 | 1.147541 | 64.1 | 1.5163 |
| 18* | −2.86885 | 0.532787 | | |
| 19 | ∞ | 0.737705 | 64.1 | 1.5163 |
| 20 | ∞ | 0.573770 | 64.1 | 1.5163 |
| 21 | ∞ | 0.000000 | | |
| IMG | ∞ | 0.000000 | | |

Aspherical Data
Fifth Surface
K=0.000000, A4=0.177750E-01, A6=0.514143E-01, A8=−0.146876E+00, A10=0.966753E-01
Sixth Surface
K=−10.486544, A4=0.181585E+00, A6=−0.961834E-01, A8=0.249683E-01, A10=−0.257298E-02
Eighteenth Surface
K=0.000000, A4=0.177810E+00, A6=−0.137418E+00, A8=0.137236E+00, A10=−0.190231E-01

The values in this example are as follows. Accordingly, it is clear that conditional expressions (1) to (4) are satisfied.

$fn = -0.892$ $fp = 3.049$ $\phi n = -1.121$ $\phi p = 0.328$ $\nu n = 40.8$ $\nu p = 18.9$ $|\phi n|/\nu n = 0.027$ $|\phi p|/\nu p = 0.017$ $(|\phi n|/\nu n)/(|\phi p|/\nu p)=1.584$ $\alpha=45.2°$ The apex α is located 5.03 mm away from the first surface 11 toward the front object P side.

With regard to the specifications in this example, the maximum forward half field angle is 74°, the half field angle of the lateral principal ray ranges between 75° and 116°, the focal length (forward light path) is 0.566 mm, the F number (forward light path) is 5.0, the maximum image height is 1.0 mm, and the maximum forward image height is 0.607 mm.

Next, a third example of the wide-angle optical system 3 according to this embodiment will be described below with reference to FIGS. 9 to 11 and lens data.

Figure 9:
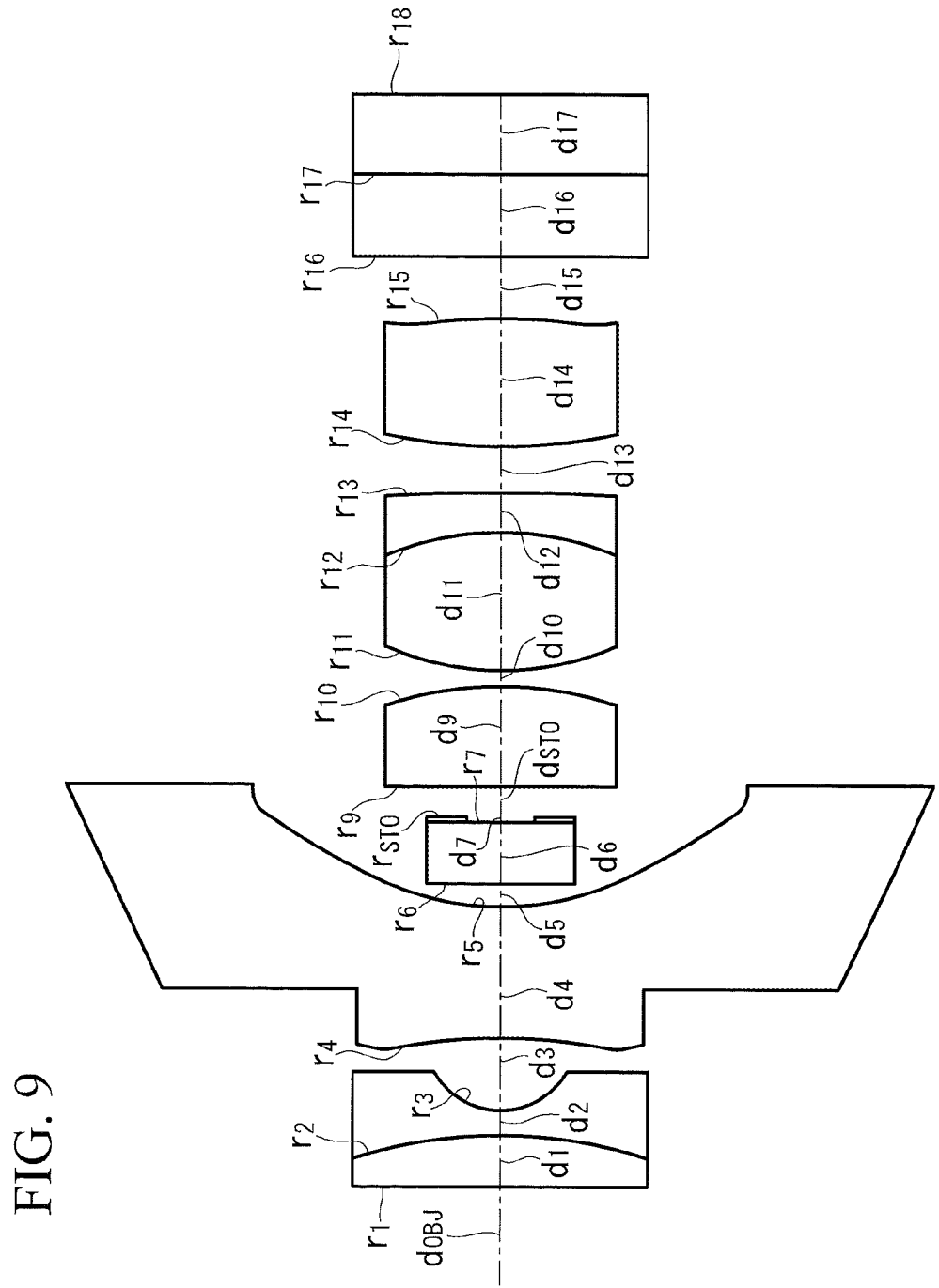
FIG. 9 illustrates the lens arrangement in a third example of the wide-angle optical system in FIG. 2.
Figure 10A:
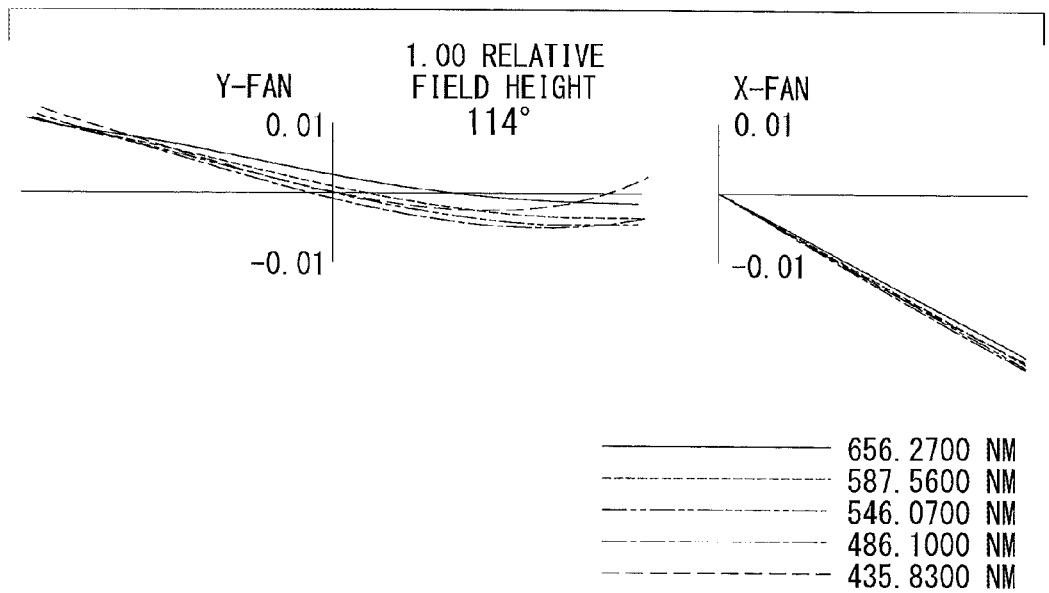
FIG. 10A is an aberration diagram of light from a lateral object in the wide-angle optical system in FIG. 9 and illustrates a case where the half field angle of a principal ray at the minimum field angle is 114°.
Figure 10B:
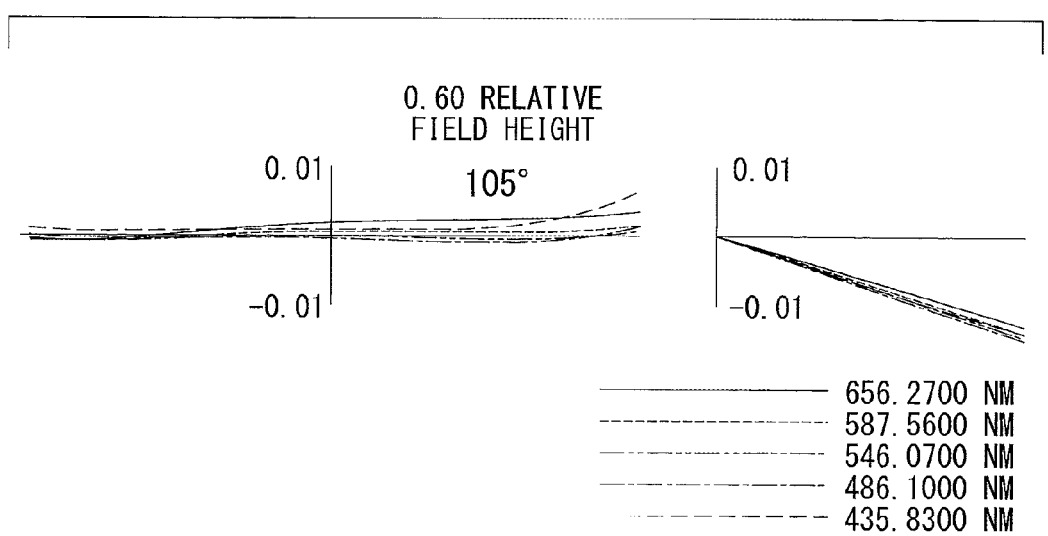
FIG. 10B is an aberration diagram of light from a lateral object in the wide-angle optical system in FIG. 9 and illustrates a case where the half field angle of a principal ray at the minimum field angle is 105°.
Figure 10C:
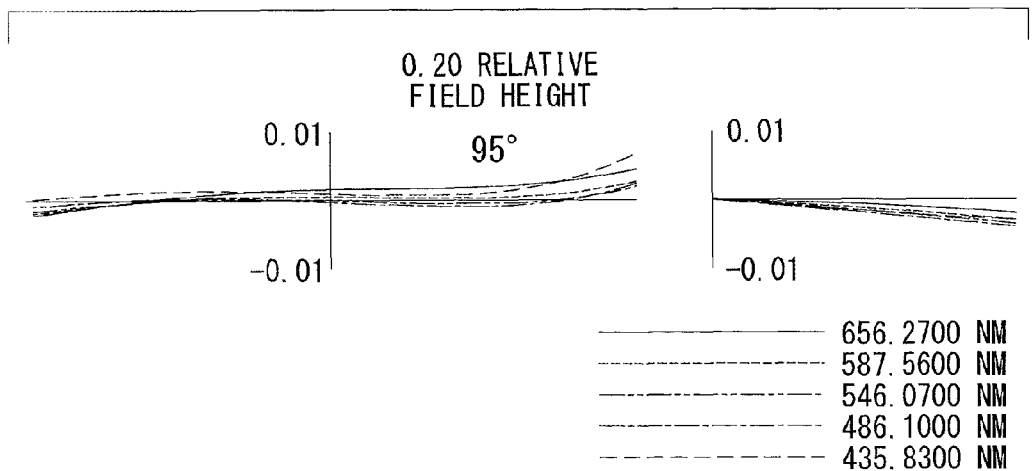
FIG. 10C is an aberration diagram of light from a lateral object in the wide-angle optical system in FIG. 9 and illustrates a case where the half field angle of a principal ray at the minimum field angle is 95°.
Figure 10D:
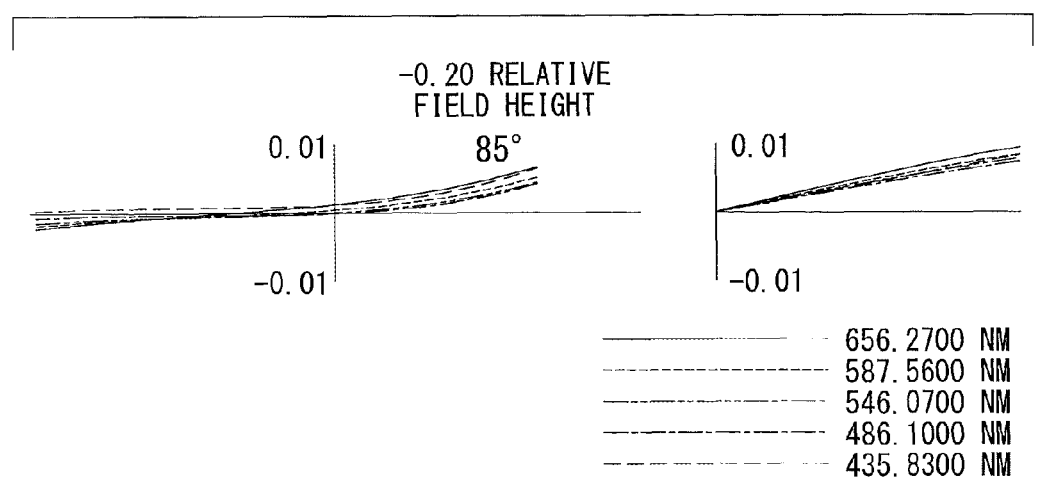
FIG. 10D is an aberration diagram of light from a lateral object in the wide-angle optical system in FIG. 9 and illustrates a case where the half field angle of a principal ray at the minimum field angle is 85°.
Figure 10E:
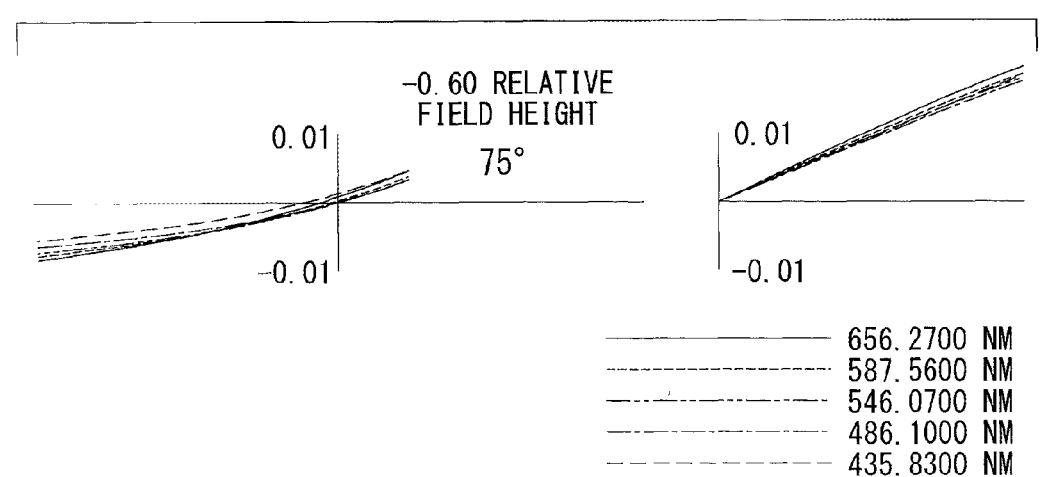
FIG. 10E is an aberration diagram of light from a lateral object in the wide-angle optical system in FIG. 9 and illustrates a case where the half field angle of a principal ray at the minimum field angle is 75°.
Figure 11A:
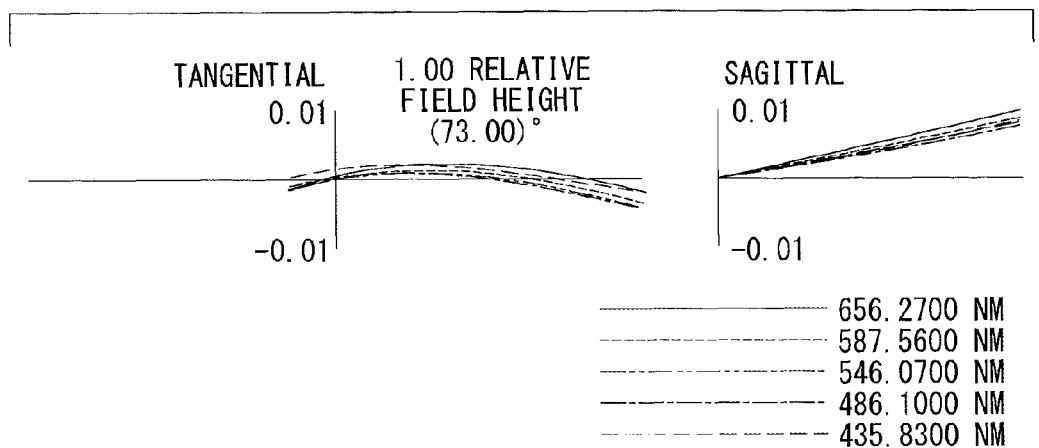
FIG. 11A is an aberration diagram of light from a front object in the wide-angle optical system in FIG. 9 and illustrates a case where the half field angle of a principal ray at the minimum field angle is 73°.
Figure 11B:
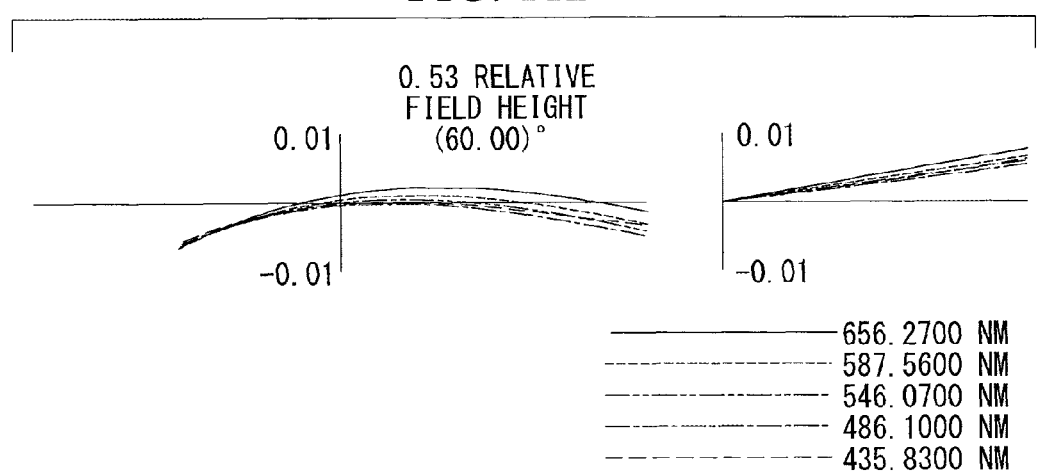
FIG. 11B is an aberration diagram of light from a front object in the wide-angle optical system in FIG. 9 and illustrates a case where the half field angle of a principal ray at the minimum field angle is 60°.
Figure 11C:
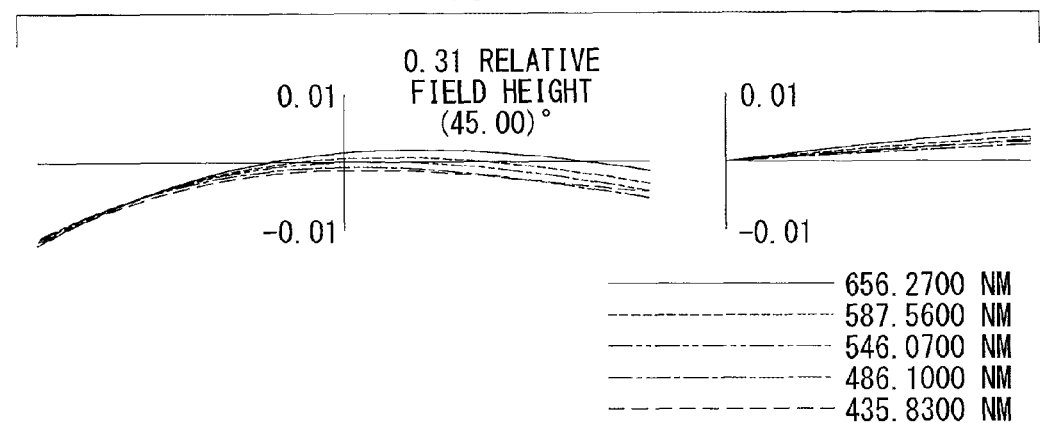
FIG. 11C is an aberration diagram of light from a front object in the wide-angle optical system in FIG. 9 and illustrates a case where the half field angle of a principal ray at the minimum field angle is 45°.
Figure 11D:
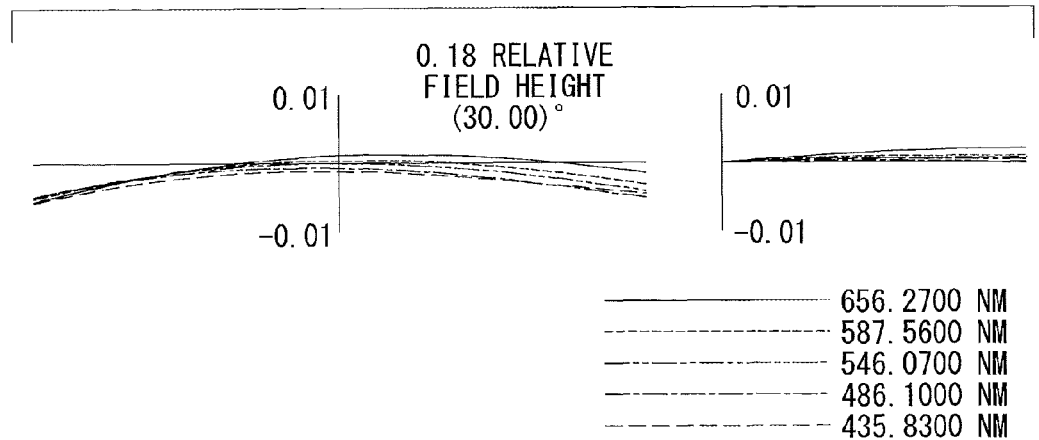
FIG. 11D is an aberration diagram of light from a front object in the wide-angle optical system in FIG. 9 and illustrates a case where the half field angle of a principal ray at the minimum field angle is 30°.
Figure 11E:
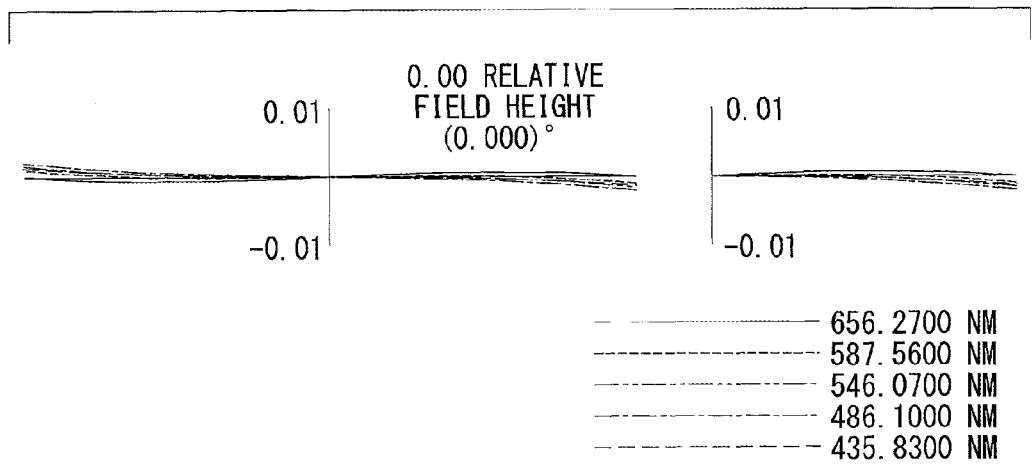
FIG. 11E is an aberration diagram of light from a front object in the wide-angle optical system in FIG. 9 and illustrates a case where the half field angle of a principal ray at the minimum field angle is 0°.

FIG. 9 illustrates the lens arrangement of the wide-angle optical system 3 according to this example. FIGS. 10A to 11E illustrate aberration diagrams of the wide-angle optical system 3 according to this example. In each diagram, the X direction indicates lateral chromatic aberration, whereas the Y direction indicates comatic aberration.

| Surface No. | r | d | ν | Nd |
|---|---|---|---|---|
| OBJ | ∞ | 11.681544 | | |
| 1 | ∞ | 0.515625 | 18.9 | 1.9343 |
| 2 | −4.91864 | 0.250000 | 71.8 | 1.7682 |
| 3 | 0.80388 | 0.741094 | | |
| 4* | −3.88773 | 1.333333 | 64.1 | 1.5163 |
| 5* | 2.57540 | 0.250420 | | |
| 6 | ∞ | 0.625000 | 64.1 | 1.5163 |
| 7 | ∞ | 0.050000 | | |
| STO | ∞ | 0.310778 | | |
| 9 | 786.25122 | 1.015625 | 46.6 | 1.8160 |
| 10 | −3.62923 | 0.166667 | | |
| 11 | 3.00000 | 1.406250 | 46.6 | 1.8160 |
| 12 | −2.98777 | 0.390625 | 18.9 | 1.9343 |
| 13 | −65.80744 | 0.477509 | | |
| 14 | 4.87920 | 1.326240 | 64.1 | 1.5163 |
| 15* | −3.58578 | 0.616667 | | |
| 16 | ∞ | 0.833333 | 64.1 | 1.5163 |
| 17 | ∞ | 0.833333 | 64.1 | 1.5163 |
| 18 | ∞ | 0.000000 | | |
| IMG | ∞ | 0.000000 | | |

Aspherical Data
Fourth Surface
  K=0.000000, A4=0.808060E-01, A6=−0.622080E-01, A8=0.978987E-02, A10=0.806216E-02
Fifth Surface
  K=0.000000, A4=−0.615673E-03, A6=−0.860821E-02, A8=0.184745E-02, A10=−0.168134E-03
Fifteenth Surface
  K=0.000000, A4=0.575488E-01, A6=0.184501E-01, A8=−0.143676E-01, A10=0.806216E-02

The values in this example are as follows. Accordingly, it is clear that conditional expressions (1) to (4) are satisfied.

$fn=-0.880$ $fp=5.265$ $\phi n=-1.137$ $\phi p=0.190$ $\nu n=71.8$ $\nu p=18.9$ $|\phi n|/\nu n=0.016$ $|\phi p|/\nu p=0.010$ $(|\phi n|/\nu n)/(|\phi p|/\nu p)=1.575$ $\alpha=50.5°$ The apex α is located 7 mm away from the first surface 11 toward the front object P side.

With regard to the specifications in this example, the maximum forward half field angle is 73°, the half field angle of the lateral principal ray ranges between 73° and 114°, the focal length (forward light path) is 0.574 mm, the F number (forward light path) is 3.0, the maximum image height is 1.0 mm, and the maximum forward image height is 0.612 mm.

Next, a fourth example of the wide-angle optical system 3 according to this embodiment will be described below with reference to FIGS. 12 to 14E and lens data.

Figure 12:
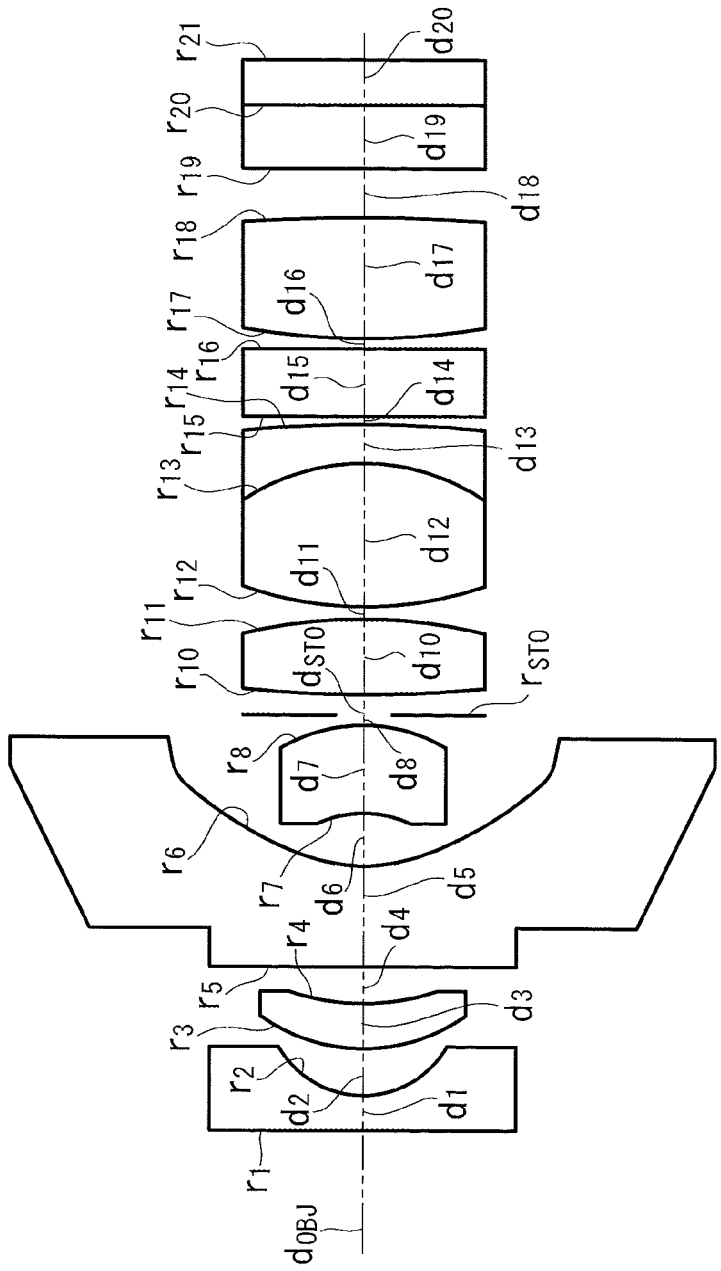
FIG. 12 illustrates the lens arrangement in a fourth example of the wide-angle optical system in FIG. 2.
Figure 13A:
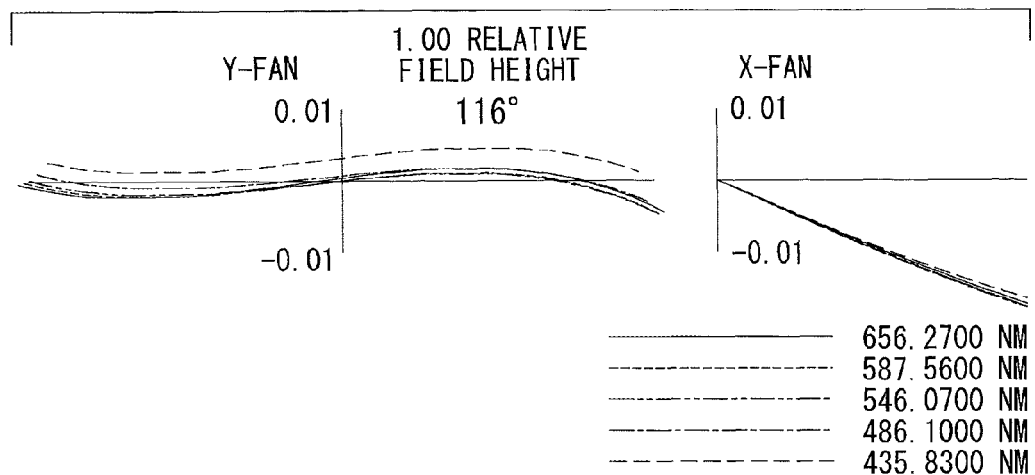
FIG. 13A is an aberration diagram of light from a lateral object in the wide-angle optical system in FIG. 12 and illustrates a case where the half field angle of a principal ray at the minimum field angle is 116°.
Figure 13B:
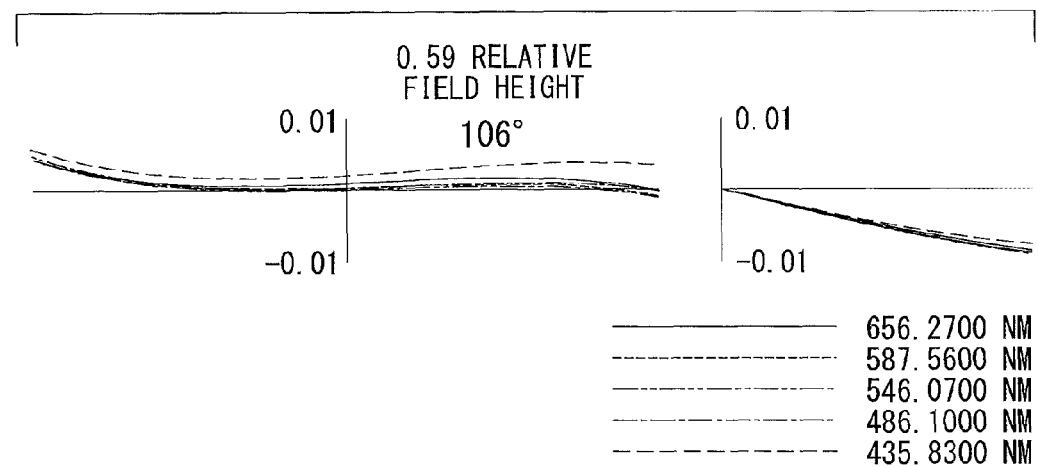
FIG. 13B is an aberration diagram of light from a lateral object in the wide-angle optical system in FIG. 12 and illustrates a case where the half field angle of a principal ray at the minimum field angle is 106°.
Figure 13C:
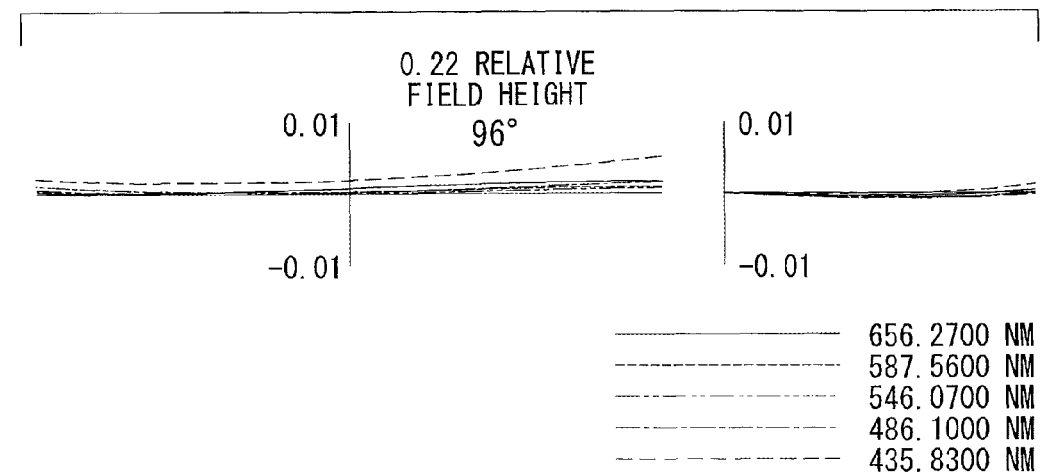
FIG. 13C is an aberration diagram of light from a lateral object in the wide-angle optical system in FIG. 12 and illustrates a case where the half field angle of a principal ray at the minimum field angle is 96°.
Figure 13D:
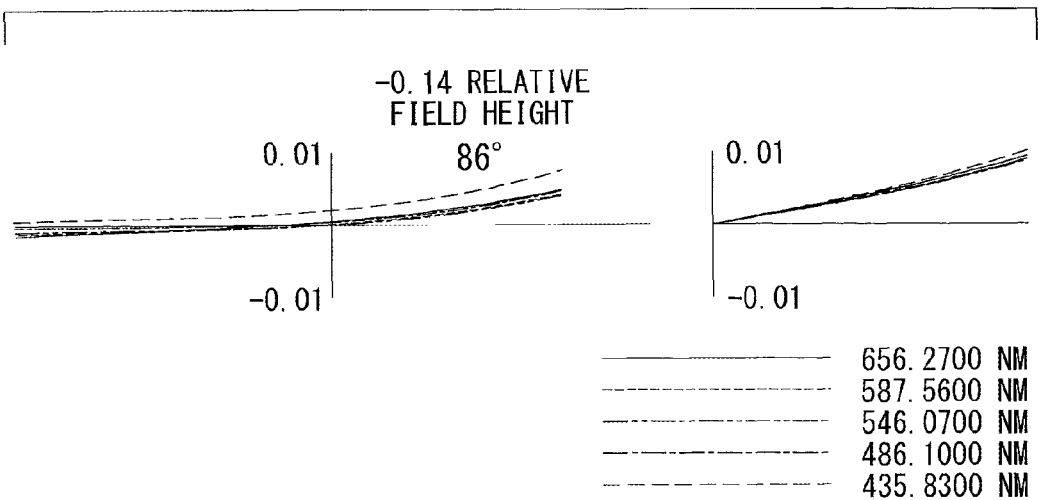
FIG. 13D is an aberration diagram of light from a lateral object in the wide-angle optical system in FIG. 12 and illustrates a case where the half field angle of a principal ray at the minimum field angle is 86°.
Figure 13E:
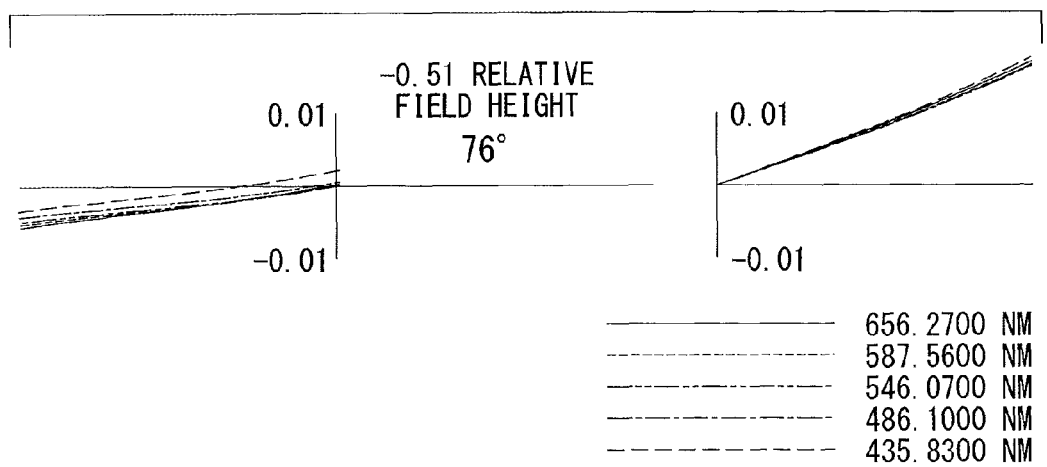
FIG. 13E is an aberration diagram of light from a lateral object in the wide-angle optical system in FIG. 12 and illustrates a case where the half field angle of a principal ray at the minimum field angle is 76°.
Figure 14A:
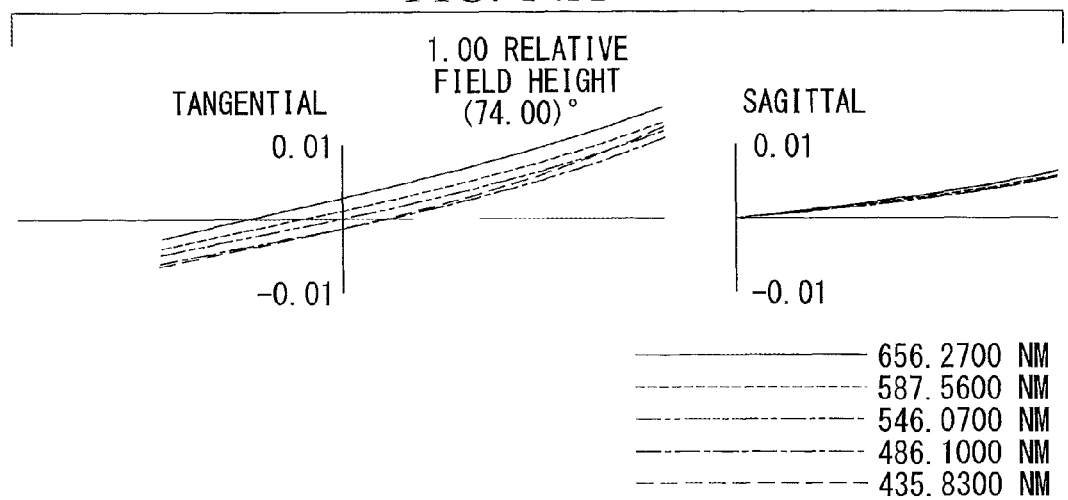
FIG. 14A is an aberration diagram of light from a front object in the wide-angle optical system in FIG. 12 and illustrates a case where the half field angle of a principal ray at the minimum field angle is 74°.
Figure 14B:
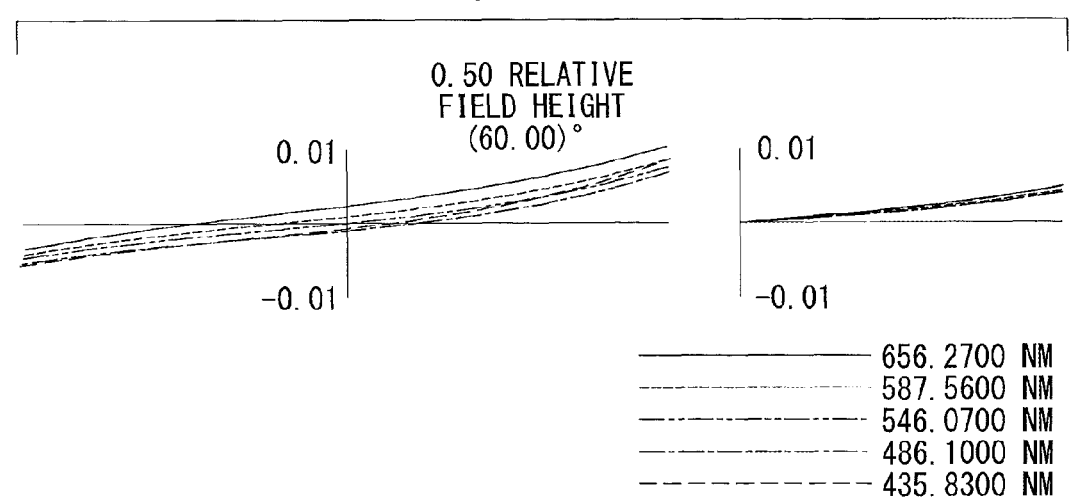
FIG. 14B is an aberration diagram of light from a front object in the wide-angle optical system in FIG. 12 and illustrates a case where the half field angle of a principal ray at the minimum field angle is 60°.
Figure 14C:
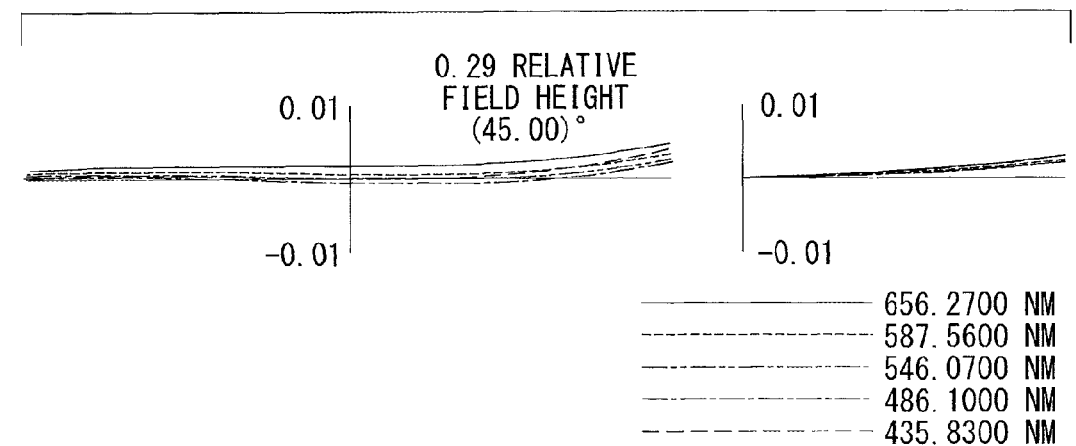
FIG. 14C is an aberration diagram of light from a front object in the wide-angle optical system in FIG. 12 and illustrates a case where the half field angle of a principal ray at the minimum field angle is 45°.
Figure 14D:
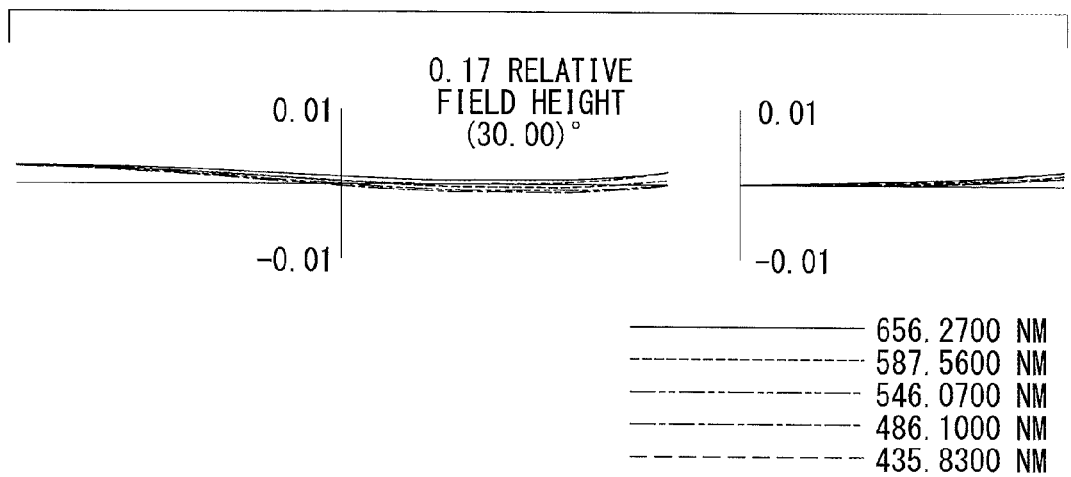
FIG. 14D is an aberration diagram of light from a front object in the wide-angle optical system in FIG. 12 and illustrates a case where the half field angle of a principal ray at the minimum field angle is 30°.
Figure 14E:
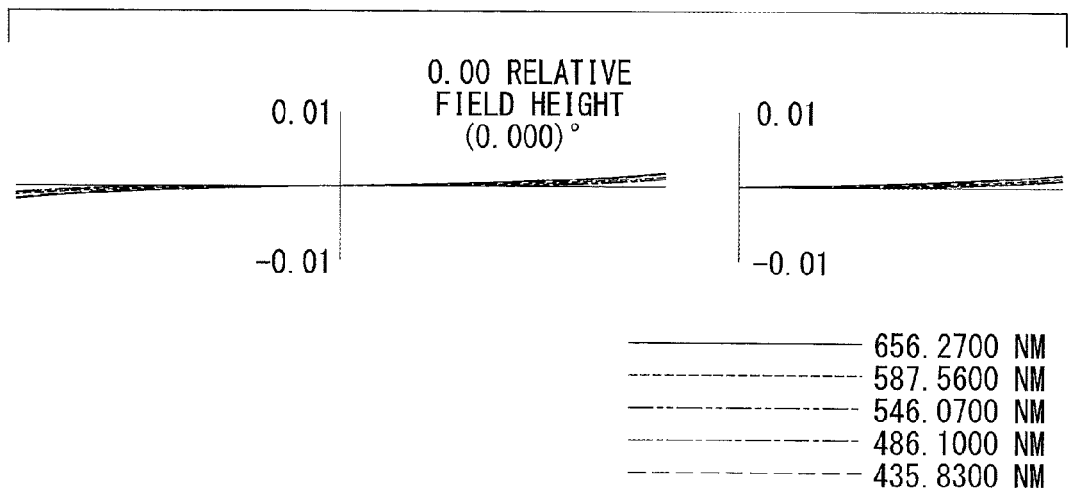
FIG. 14E is an aberration diagram of light from a front object in the wide-angle optical system in FIG. 12 and illustrates a case where the half field angle of a principal ray at the minimum field angle is 0°.

FIG. 12 illustrates the lens arrangement of the wide-angle optical system 3 according to this example. FIGS. 13A to 14E illustrate aberration diagrams of the wide-angle optical system 3 according to this example. In each diagram, the X direction indicates lateral chromatic aberration, whereas the Y direction indicates comatic aberration.

| Surface No. | r | d | ν | Nd |
|---|---|---|---|---|
| OBJ | ∞ | 8.379325 | | |
| 1 | ∞ | 0.335196 | 40.8 | 1.8830 |
| 2 | 1.00847 | 0.469274 | | |
| 3 | 1.73184 | 0.470085 | 17.4 | 1.9591 |
| 4 | 2.91464 | 0.351955 | | |
| 5* | −11.88457 | 1.005587 | 64.1 | 1.5163 |
| 6* | 1.82961 | 0.525140 | | |
| 7 | −1.64469 | 0.883901 | 46.6 | 1.8160 |
| 8 | −1.81306 | 0.111732 | | |
| STO | ∞ | 0.209578 | | |
| 10 | 14.52514 | 0.782119 | 46.6 | 1.8160 |
| 11 | −5.00980 | 0.111732 | | |
| 12 | 4.00733 | 1.428177 | 46.6 | 1.8160 |
| 13 | −2.27022 | 0.391061 | 17.4 | 1.9591 |
| 14 | −12.63447 | 0.111732 | | |
| 15 | ∞ | 0.670391 | 64.1 | 1.5163 |
| 16 | ∞ | 0.111732 | | |
| 17 | 8.45282 | 1.184413 | 40.9 | 1.8061 |
| 18* | −21.83998 | 0.525140 | | |
| 19 | ∞ | 0.636872 | 64.1 | 1.5163 |
| 20 | ∞ | 0.558659 | 64.1 | 1.5163 |
| 21 | ∞ | 0.000000 | | |
| IMG | ∞ | 0.000000 | | |

Aspherical Data
Fifth Surface
  K=0.000000, A4=0.716898E-01, A6=−0.689122E-01, A8=0.574472E-02, A10=0.204598E-01
Sixth Surface
  K=−0.130259, A4=0.531045E-01, A6=−0.689122E-01, A8=0.212911E-01, A10=−0.279626E-02
Eighteenth Surface
  K=0.000000, A4=−0.409946E-02, A6=0.610747E-01, A8=−0.368003E-01, A10=0.796250E-03

The values in this example are as follows. Accordingly, it is clear that conditional expressions (1) to (4) are satisfied.

$fn=-1.135$ $fp=3.672$ $\phi n=-0.881$ $\phi p=0.272$ $\nu n=40.8$

νp=17.4

|φn|/νn=0.022

|φp|/νp=0.016

(|φn|/νn)/(|φp|/νp)=1.379

α=50°

The apex α is located 6.81 mm away from the first surface 11 toward the front object P side.

With regard to the specifications in this example, the maximum forward half field angle is 75°, the half field angle of the lateral principal ray ranges between 76° and 115°, the focal length (forward light path) is 0.702 mm, the F number (forward light path) is 4.7, the maximum image height is 1.0 mm, and the maximum forward image height is 0.646 mm.

Next, a fifth example of the wide-angle optical system 3 according to this embodiment will be described below with reference to FIGS. 15 to 17E and lens data.

Figure 15:
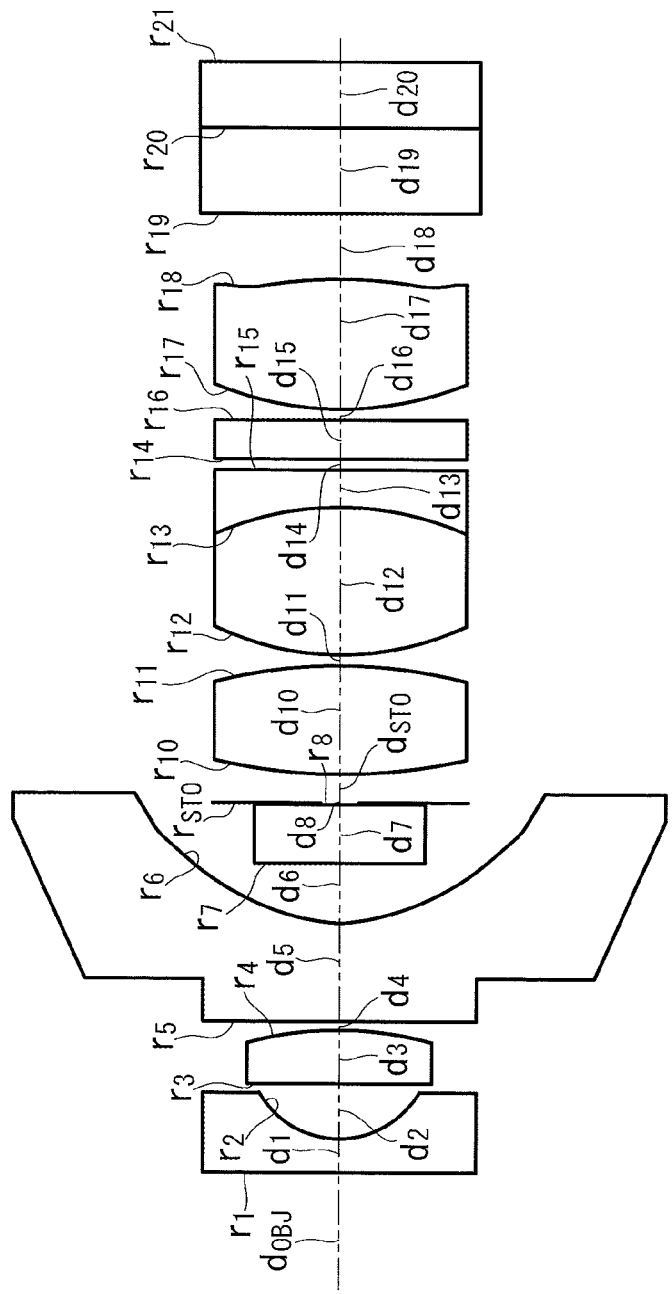
FIG. 15 illustrates the lens arrangement in a fifth example of the wide-angle optical system in FIG. 2.
Figure 16A:
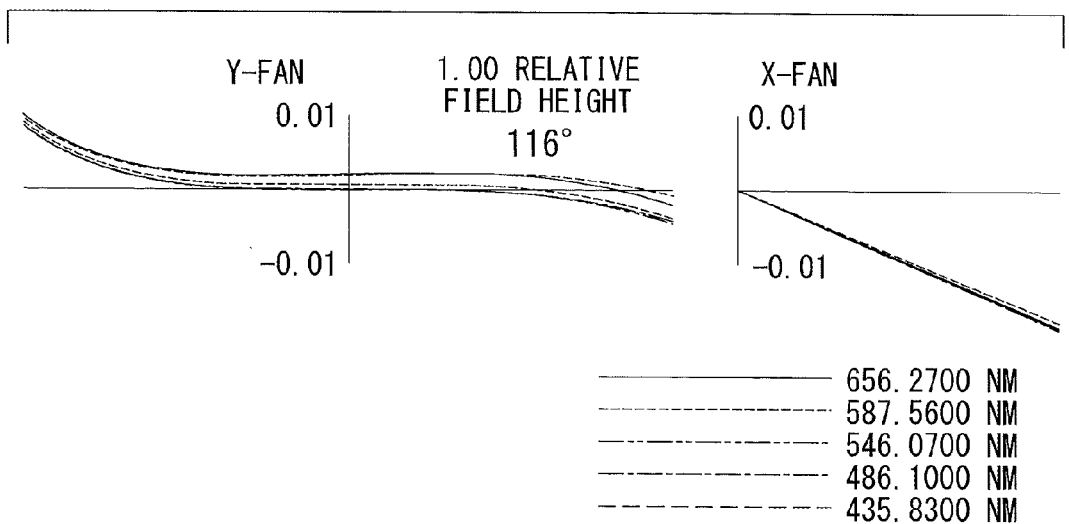
FIG. 16A is an aberration diagram of light from a lateral object in the wide-angle optical system in FIG. 15 and illustrates a case where the half field angle of a principal ray at the minimum field angle is 116°.
Figure 16B:
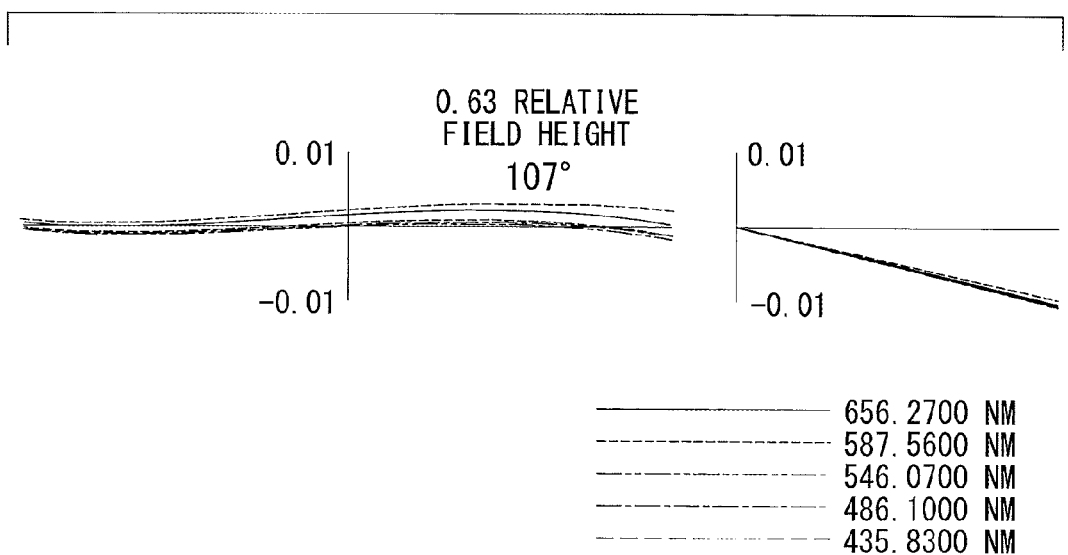
FIG. 16B is an aberration diagram of light from a lateral object in the wide-angle optical system in FIG. 15 and illustrates a case where the half field angle of a principal ray at the minimum field angle is 107°.
Figure 16C:
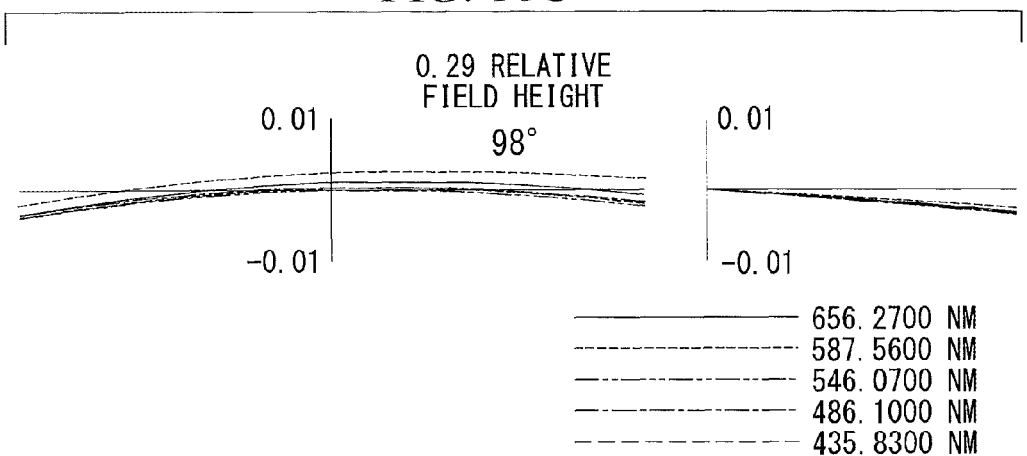
FIG. 16C is an aberration diagram of light from a lateral object in the wide-angle optical system in FIG. 15 and illustrates a case where the half field angle of a principal ray at the minimum field angle is 98°.
Figure 16D:
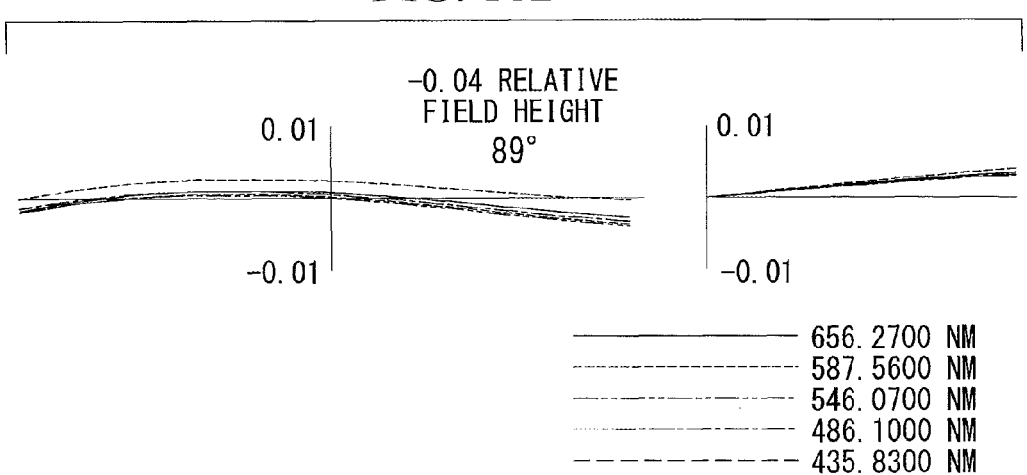
FIG. 16D is an aberration diagram of light from a lateral object in the wide-angle optical system in FIG. 15 and illustrates a case where the half field angle of a principal ray at the minimum field angle is 89°.
Figure 16E:
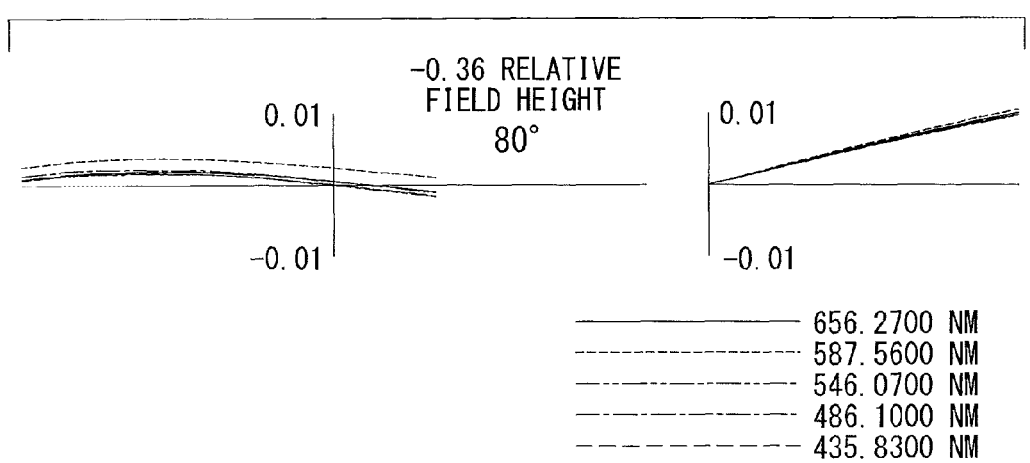
FIG. 16E is an aberration diagram of light from a lateral object in the wide-angle optical system in FIG. 15 and illustrates a case where the half field angle of a principal ray at the minimum field angle is 80°.
Figure 17A:
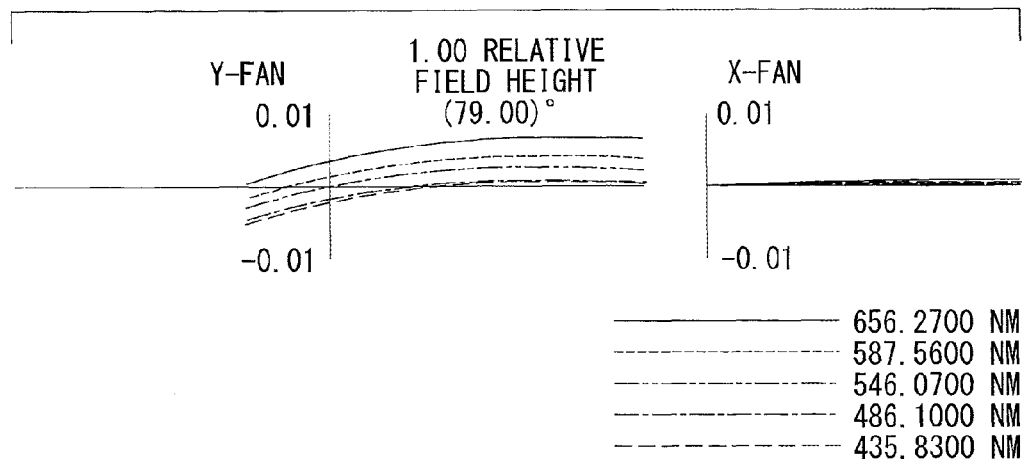
FIG. 17A is an aberration diagram of light from a front object in the wide-angle optical system in FIG. 15 and illustrates a case where the half field angle of a principal ray at the minimum field angle is 79°.
Figure 17B:
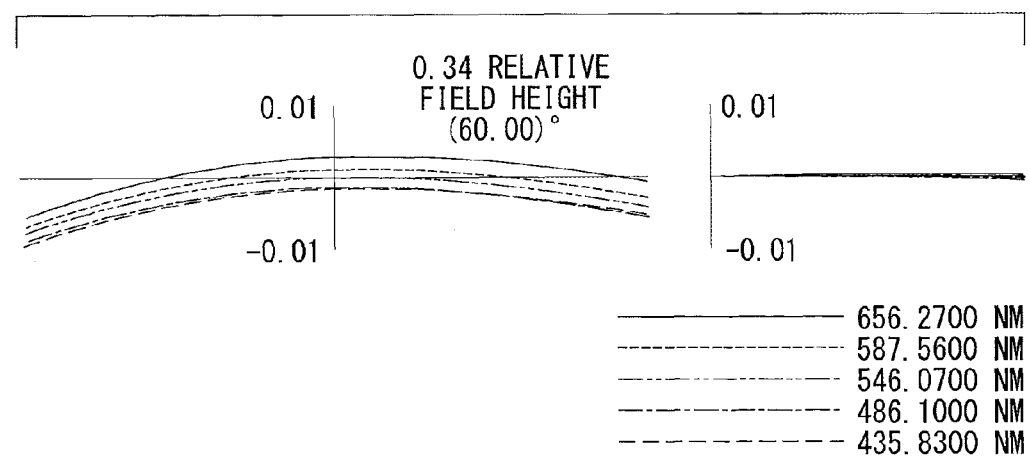
FIG. 17B is an aberration diagram of light from a front object in the wide-angle optical system in FIG. 15 and illustrates a case where the half field angle of a principal ray at the minimum field angle is 60°.
Figure 17C:
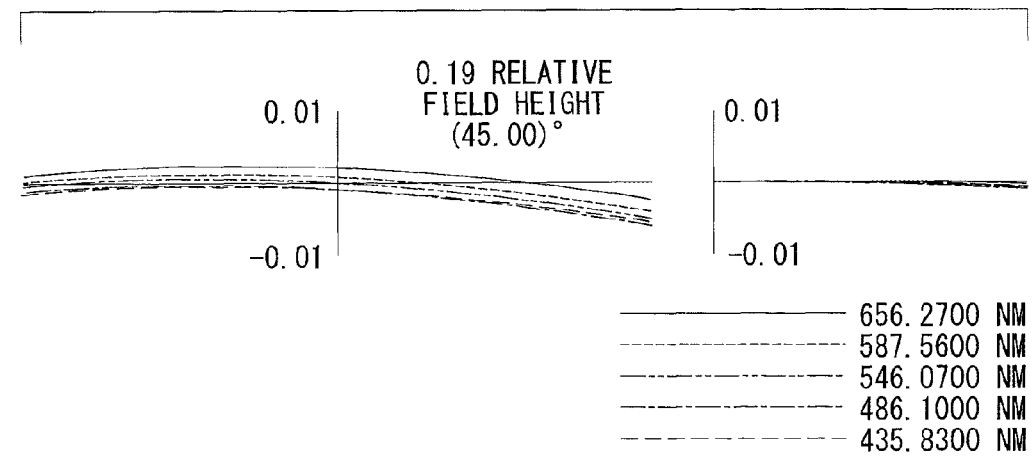
FIG. 17C is an aberration diagram of light from a front object in the wide-angle optical system in FIG. 15 and illustrates a case where the half field angle of a principal ray at the minimum field angle is 45°.
Figure 19A:
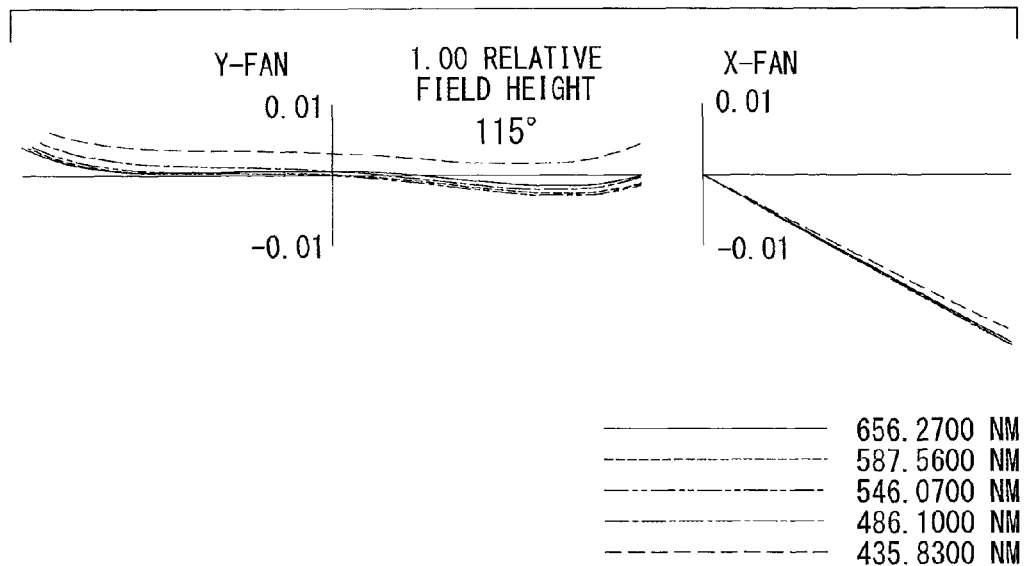
FIG. 19A is an aberration diagram of light from a lateral object in the wide-angle optical system in FIG. 18 and illustrates a case where the half field angle of a principal ray at the minimum field angle is 115°.
Figure 19B:
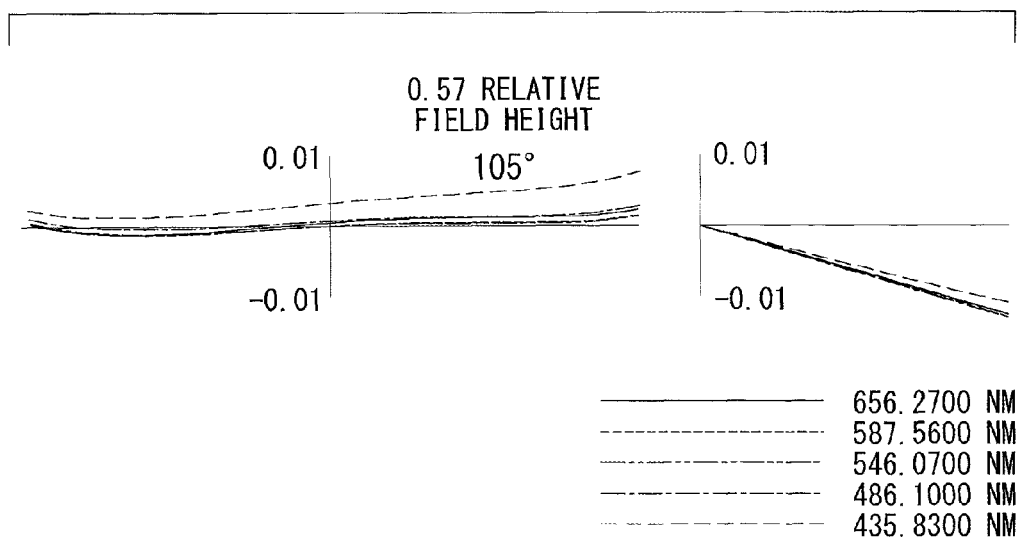
FIG. 19B is an aberration diagram of light from a lateral object in the wide-angle optical system in FIG. 18 and illustrates a case where the half field angle of a principal ray at the minimum field angle is 105°.
Figure 19C:
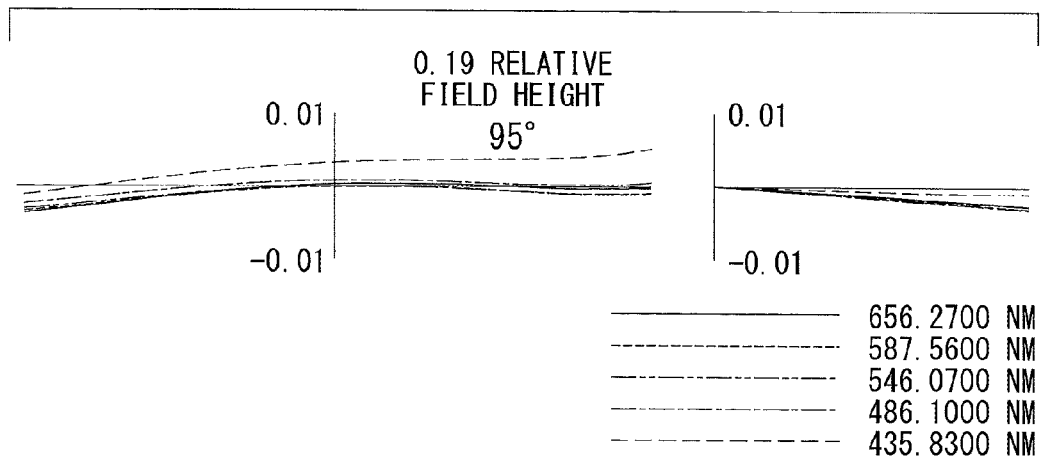
FIG. 19C is an aberration diagram of light from a lateral object in the wide-angle optical system in FIG. 18 and illustrates a case where the half field angle of a principal ray at the minimum field angle is 95°.
Figure 19D:
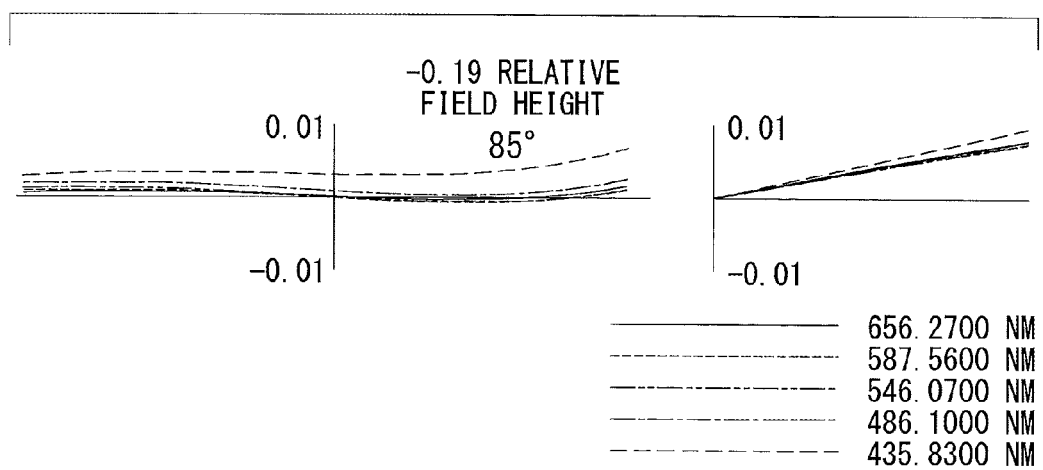
FIG. 19D is an aberration diagram of light from a lateral object in the wide-angle optical system in FIG. 18 and illustrates a case where the half field angle of a principal ray at the minimum field angle is 85°.
Figure 19E:
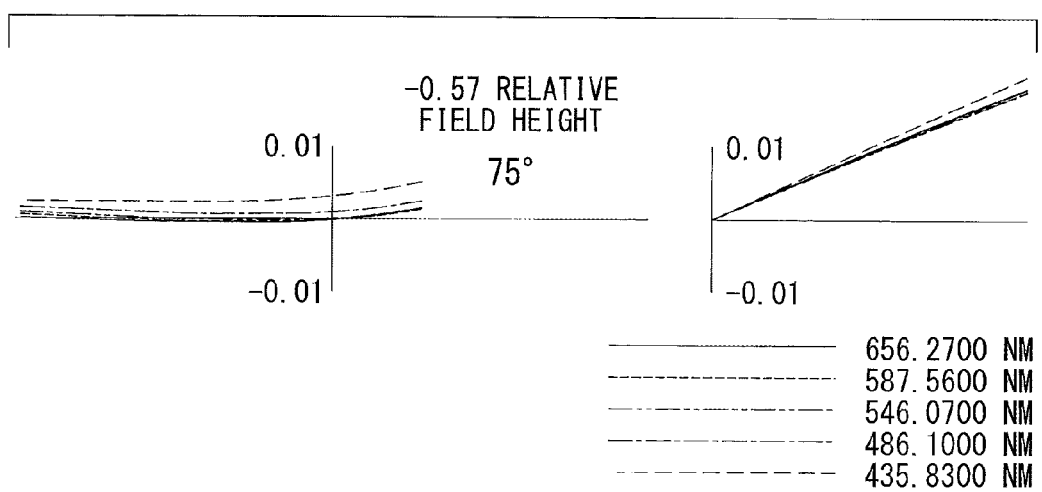
FIG. 19E is an aberration diagram of light from a lateral object in the wide-angle optical system in FIG. 18 and illustrates a case where the half field angle of a principal ray at the minimum field angle is 75°.
Figure 20A:
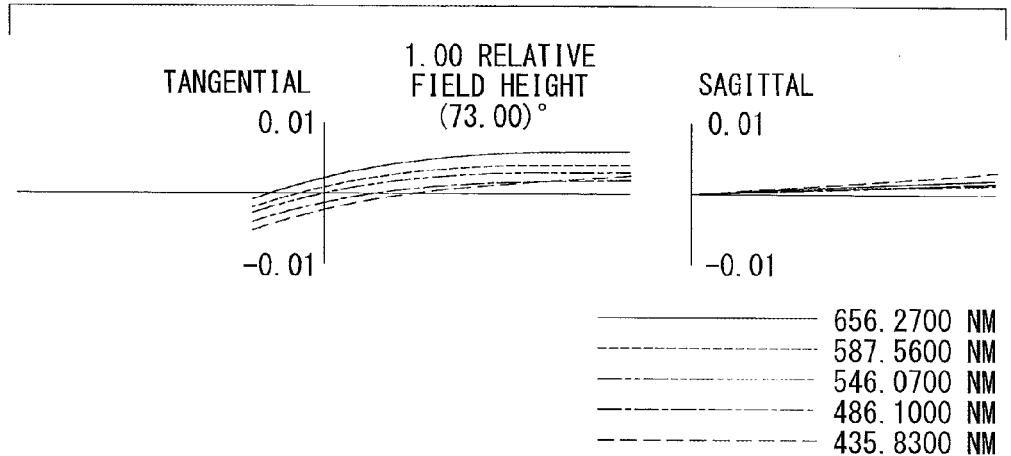
FIG. 20A is an aberration diagram of light from a front object in the wide-angle optical system in FIG. 18 and illustrates a case where the half field angle of a principal ray at the minimum field angle is 73°.
Figure 20B:
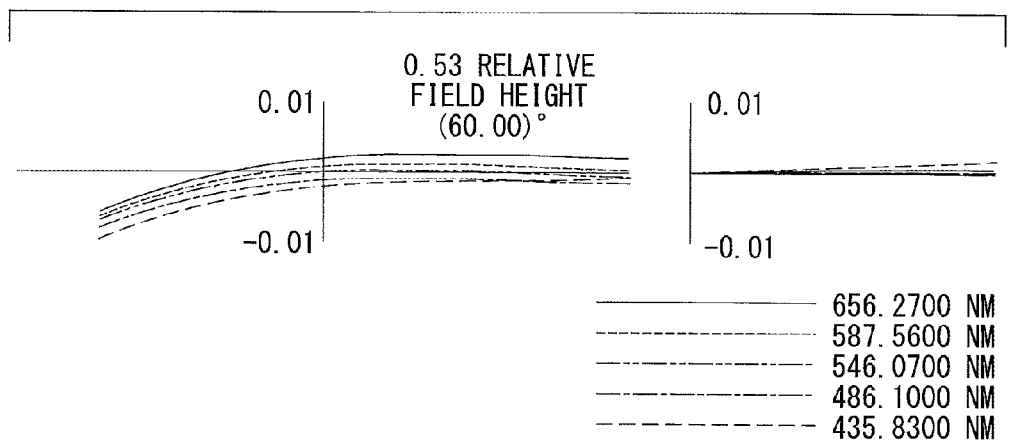
FIG. 20B is an aberration diagram of light from a front object in the wide-angle optical system in FIG. 18 and illustrates a case where the half field angle of a principal ray at the minimum field angle is 60°.
Figure 20C:
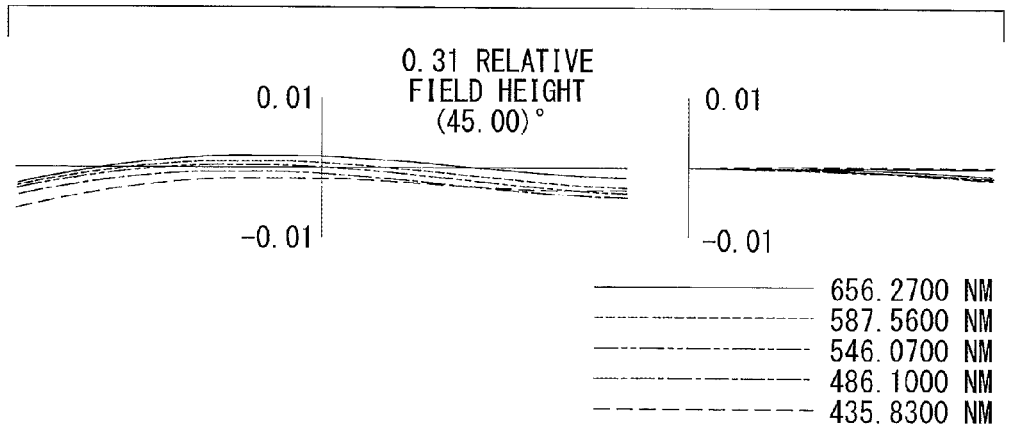
FIG. 20C is an aberration diagram of light from a front object in the wide-angle optical system in FIG. 18 and illustrates a case where the half field angle of a principal ray at the minimum field angle is 45°.
Figure 20D:
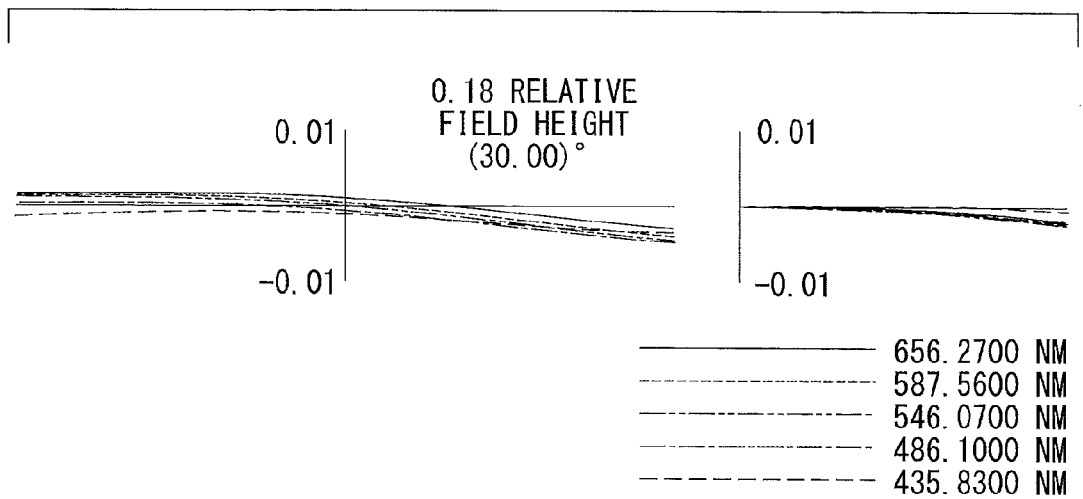
FIG. 20D is an aberration diagram of light from a front object in the wide-angle optical system in FIG. 18 and illustrates a case where the half field angle of a principal ray at the minimum field angle is 30°.
Figure 20E:
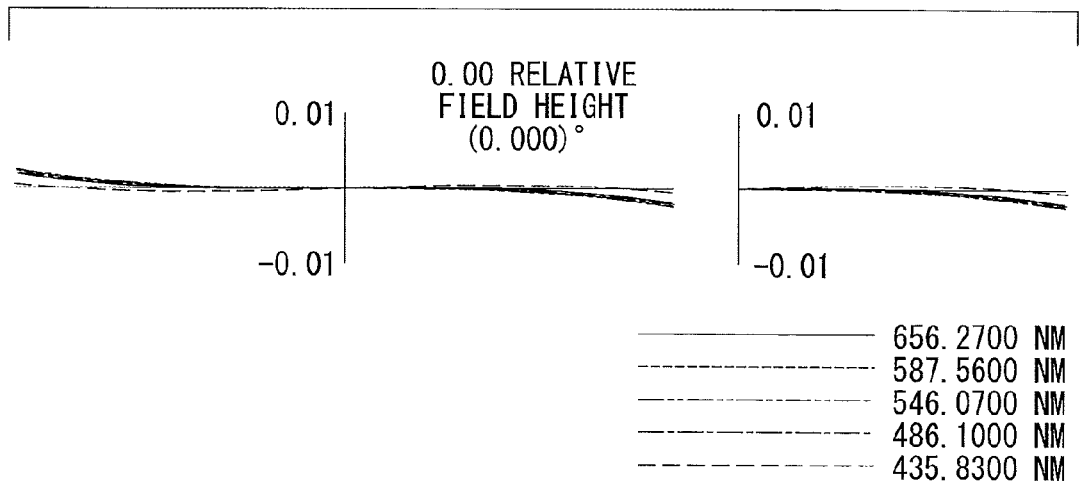
FIG. 20E is an aberration diagram of light from a front object in the wide-angle optical system in FIG. 18 and illustrates a case where the half field angle of a principal ray at the minimum field angle is 0°.

FIG. 15 illustrates the lens arrangement of the wide-angle optical system 3 according to this example. FIGS. 16A to 17E illustrate aberration diagrams of the wide-angle optical system 3 according to this example. In each diagram, the X direction indicates lateral chromatic aberration, whereas the Y direction indicates comatic aberration.

| Surface No. | r | d | ν | Nd |
|---|---|---|---|---|
| OBJ | ∞ | 6.292165 | | |
| 1 | ∞ | 0.294118 | | |
| 2 | 0.84790 | 0.487395 | 40.8 | 1.8830 |
| 3 | ∞ | 0.464607 | 18.9 | 1.9343 |
| 4 | −3.36303 | 0.084034 | | |
| 5* | −8.40336 | 0.840336 | 64.1 | 1.5163 |
| 6* | 1.22079 | 0.533938 | | |
| 7 | ∞ | 0.504202 | 64.1 | 1.5163 |
| 8 | ∞ | 0.025210 | | |
| STO | ∞ | 0.281827 | | |
| 10 | 5.09426 | 0.949580 | 47.4 | 1.7920 |
| 11 | −5.09426 | 0.130195 | | |
| 12 | 2.79328 | 1.310924 | 54.7 | 1.7292 |
| 13 | −2.79328 | 0.327731 | 18.9 | 1.9343 |
| 14 | ∞ | 0.084034 | | |
| 15 | ∞ | 0.336134 | 64.1 | 1.5163 |
| 16 | ∞ | 0.084034 | | |
| 17 | 2.89916 | 1.159664 | 64.1 | 1.5163 |
| 18* | −2.43697 | 0.554439 | | |
| 19 | ∞ | 0.756303 | 64.1 | 1.5163 |
| 20 | ∞ | 0.588235 | 64.1 | 1.5163 |
| 21 | ∞ | 0.000000 | | |
| IMG | ∞ | 0.000000 | | |

Aspherical Data
Fifth Surface
  K=0.000000, A4=0.172083E+00, A6=−0.216060E+00, A8=0.971054E-01, A10=0.000000E+00
Sixth Surface
  K=−5.101829, A4=0.770935E-01, A6=−0.124607E-01, A8=−0.617295E-02, A10=0.185243E-02
Eighteenth Surface
  K=0.000000, A4=0.159629E+00, A6=−0.124019E+00, A8=0.142429E+00, A10=−0.489314E-01

The values in this example are as follows. Accordingly, it is clear that conditional expressions (1) to (4) are satisfied.

fn=−0.955 fp=3.600

φn=−1.047

φp=0.278

νn=40.8

νp=18.9

|φn|/νn=0.026

|φp|/νp=0.015

(|φn|/νn)/(|φp|/νp)=1.747

α=48°

The apex α is located 4.71 mm away from the first surface 11 toward the front object P side.

With regard to the specifications in this example, the maximum forward half field angle is 80°, the half field angle of the lateral principal ray ranges between 80° and 116°, the focal length (forward light path) is 0.547 mm, the F number (forward light path) is 5.0, the maximum image height is 1.0 mm, and the maximum forward image height is 0.620 mm.

Next, a sixth example of the wide-angle optical system 3 according to this embodiment will be described below with reference to FIGS. 18 to 20E and lens data.

FIG. 18 illustrates the lens arrangement of the wide-angle optical system 3 according to this example. FIGS. 19A to 20E illustrate aberration diagrams of the wide-angle optical system 3 according to this example. In each diagram, the X direction indicates lateral chromatic aberration, whereas the Y direction indicates comatic aberration.

| Surface No. | r | d | ν | Nd |
|---|---|---|---|---|
| OBJ | ∞ | 19.917502 | | |
| 1 | ∞ | 0.416667 | 71.8 | 1.7682 |
| 2 | 1.12833 | 0.716667 | | |
| 3 | −3.66667 | 0.458333 | 18.9 | 1.9343 |
| 4 | −3.13864 | 0.083333 | | |
| 5* | −6.14499 | 1.500000 | 64.1 | 1.5163 |
| 6* | 2.88252 | 1.143789 | | |
| 7 | ∞ | 0.666667 | 64.1 | 1.5163 |
| 8 | ∞ | 0.050000 | | |
| STO | ∞ | 0.166667 | | |
| 10 | 10.50000 | 1.133333 | 46.6 | 1.8160 |
| 11 | −6.47879 | 0.166667 | | |
| 12 | 3.75000 | 1.681428 | 46.6 | 1.8160 |
| 13 | −3.22553 | 0.416667 | 18.9 | 1.9343 |
| 14 | 22.71414 | 0.166667 | | |
| 15 | 3.33333 | 1.350000 | 64.1 | 1.5163 |
| 16* | −3.14155 | 0.583333 | | |
| 17 | ∞ | 0.833333 | 64.1 | 1.5163 |
| 18 | ∞ | 0.833333 | 64.1 | 1.5163 |
| 19 | ∞ | 0.000000 | | |
| IMG | ∞ | 0.000000 | | |

Aspherical Data
Fifth Surface
  K=0.000000, A4=0.488513E-01, A6=−0.232544E-01, A8=0.396655E-02, A10=0.134335E-03
Sixth Surface
  K=0.000000, A4=0.210465E-02, A6=−0.518526E-02, A8=0.848642E-03, A10=−0.604811E-04
Eighteenth Surface
  K=0.000000, A4=0.428587E-01, A6=0.308236E-01, A8=−0.279936E-01, A10=0.868532E-02

The values in this example are as follows. Accordingly, it is clear that conditional expressions (1) to (4) are satisfied.

fn=−1.464 fp=16.437

$\phi n = -0.683$ $\phi p = 0.061$ $\nu n = 71.8$ $\nu p = 18.9$ $|\phi n|/\nu n = 0.010$ $|\phi p|/\nu p = 0.003$ $(|\phi n|/\nu n)/(|\phi p|/\nu p) = 2.955$ $\alpha = 50.5°$ The apex α is located 7.33 mm away from the first surface 11 toward the front object P side.

With regard to the specifications in this example, the maximum forward half field angle is 73.5°, the half field angle of the lateral principal ray ranges between 74° and 116°, the focal length (forward light path) is 0.588 mm, the F number (forward light path) is 3.0, the maximum image height is 1.0 mm, and the maximum forward image height is 0.623 mm.

As a result, the above-described embodiments lead to the following aspects.

That is, as aspect of the present invention provides a wide-angle optical system including a first group having a negative lens with negative refractive power and a positive lens with positive refractive power; a second group having a catadioptric optical element disposed at an image side of the first group; and a third group having positive refractive power and disposed at the image side of the second group. The catadioptric optical element includes a first surface disposed at an object side, a second surface disposed at the image side, and a third surface. The first surface includes a first transmission surface having an optical axis in the center thereof and a first reflection surface that is disposed in a ring shape around the first transmission surface and that reflects light from the image side. The second surface includes a second transmission surface having an optical axis in the center thereof and a second reflection surface that is disposed in a ring shape around the second transmission surface and that reflects light from the object side. The third surface is a circular conical transmission surface that is disposed between the first surface and the second surface and an apex of which is located at the object side.

Expressions (1), (2), and (3) below are satisfied:

$$\nu n > \nu p \quad (1)$$

$$|\phi n| > |\phi p| \quad (2)$$

$$\alpha/2 > 90° - \theta k \quad (3)$$

where νn denotes an Abbe number of the negative lens, νp denotes an Abbe number of the positive lens, φn denotes the refractive power of the negative lens, φp denotes the refractive power of the positive lens, α denotes an apex angle of the third surface, and θk denotes a half field angle of a principal ray at a minimum field angle within a lateral field of view and satisfies 0°<θk<90°.

According to this aspect, when light from a front object enters the first group, the light passes through the negative lens with the large Abbe number and the positive lens with the small Abbe number. By setting a large value for the Abbe number of the negative lens, in which lateral chromatic aberration tends to occur easily, the occurrence of lateral chromatic aberration in the light passing through the first group can be suppressed. The light that has passed through the first group then passes through the first transmission surface and the second transmission surface in the second group and is subsequently focused by the third group.

Light from a lateral object becomes incident on the third surface in the second group without entering the first group. In this case, the light incident on the third surface satisfies expression (3) so that all principal rays thereof enter from the image side relative to the normal to the third surface and are refracted toward the image side. As a result, the signs of lateral chromatic aberrations occurring in all light rays from the lateral object can be made the same as the sign of lateral chromatic aberration occurring in the light from the front object. The lateral light refracted toward the image side at the third surface is sequentially reflected once at the second reflection surface of the second surface and once at the first reflection surface of the first surface and subsequently passes through the second transmission surface of the second surface so as to be focused by the third group.

Specifically, because the signs of lateral chromatic aberrations in the two light rays that are to enter the third group from the front and lateral objects are the same, the lateral chromatic aberrations of all light rays can be sufficiently corrected using the single third group.

Since the light from the lateral object is reflected twice within the catadioptric optical element, an image in the lateral field of view is prevented from being vertically inverted. Consequently, the directions of images in all fields of view can be aligned.

In the above-described aspect, the negative lens and the positive lens in the first group may satisfy expression (4) below:

$$\nu n > 35 > \nu p \quad (4)$$

Another aspect of the present invention provides an endoscope including the aforementioned wide-angle optical system.

According to this aspect, it is possible to acquire a wide-angle endoscopic image in which lateral chromatic aberration is sufficiently corrected.

Advantageous Effects of Invention

According to the present invention, lateral chromatic aberration can be sufficiently corrected by a single optical element in a subsequent stage while aligning the directions of images in all fields of view.

REFERENCE SIGNS LIST 1 endoscope
3 wide-angle optical system
4 negative lens
5 positive lens
6 first group
7 second group
8 third group
11 first surface
11a first transmission surface
11b first reflection surface
12 second surface
12a second transmission surface
12b second reflection surface
13 third surface
14 catadioptric optical element

The invention claimed is:

1. A wide-angle optical system consisting of:
   a first group consisting of a single negative lens with negative refractive power and a single positive lens with positive refractive power;
   a catadioptric optical element disposed at an image side of the first group; and
   a third group having positive refractive power and disposed at the image side of the catadioptric optical element,
   wherein the catadioptric optical element includes a first surface disposed at an object side, a second surface disposed at the image side, and a third surface, wherein the first surface includes a first transmission surface having an optical axis in the center thereof and a first reflection surface that is disposed in a ring shape around the first transmission surface and that reflects light from the image side, wherein the second surface includes a second transmission surface having an optical axis in the center thereof and a second reflection surface that is disposed in a ring shape around the second transmission surface and that reflects light from the object side, and wherein the third surface is a circular conical transmission surface that is disposed between the first surface and the second surface and an apex of which is located at the object side, and
   wherein expressions (1), (2), and (3) below are satisfied:

$$\nu n > \nu p \quad (1)$$

$$|\phi n| > |\phi p| \quad (2)$$

$$\alpha/2 > 90° - \theta k \quad (3)$$

where $\nu n$ denotes an Abbe number of the negative lens, $\nu p$ denotes an Abbe number of the positive lens, $\phi n$ denotes the refractive power of the negative lens, $\phi p$ denotes the refractive power of the positive lens, $\alpha$ denotes an apex angle of the third surface, and $\theta k$ denotes a half field angle of a principal ray at a minimum field angle within a lateral field of view and satisfies $0° < \theta k < 90°$.

2. The wide-angle optical system according to claim 1, wherein the negative lens and the positive lens in the first group satisfy expression (4) below:

$$\nu n > 35 > \nu p \quad (4).$$

3. An endoscope comprising the wide-angle optical system according to claim 1.

* * * * *